(12) United States Patent
Handler

(10) Patent No.: US 12,402,791 B2
(45) Date of Patent: *Sep. 2, 2025

(54) PATIENT PHYSIOLOGICAL MONITOR MOUNTING DETECTION

(71) Applicant: Drägerwerk AG & Co. KGaA, Lübeck (DE)

(72) Inventor: Matthew Bryan Handler, Beverly, MA (US)

(73) Assignee: Drägerwerk AG & Co. KGaA, Lübeck (DE)

( * ) Notice: Subject to any disclaimer, the term of this patent is extended or adjusted under 35 U.S.C. 154(b) by 0 days.

This patent is subject to a terminal disclaimer.

(21) Appl. No.: 18/761,678

(22) Filed: Jul. 2, 2024

(65) Prior Publication Data

US 2024/0350009 A1    Oct. 24, 2024

Related U.S. Application Data

(63) Continuation of application No. 17/350,512, filed on Jun. 17, 2021, now Pat. No. 12,048,506.

(60) Provisional application No. 63/106,640, filed on Oct. 28, 2020.

(51) Int. Cl.
*G01D 5/12* (2006.01)
*A61B 5/00* (2006.01)
*H01R 13/641* (2006.01)

(52) U.S. Cl.
CPC .......... *A61B 5/0017* (2013.01); *A61B 5/6801* (2013.01); *G01D 5/12* (2013.01); *A61B 2560/0456* (2013.01); *A61B 2562/0223* (2013.01); *H01R 13/641* (2013.01)

(58) Field of Classification Search
None
See application file for complete search history.

(56) References Cited

U.S. PATENT DOCUMENTS

| 8,172,752 B2 * | 5/2012 | Russ | H04M 1/725 |
| | | | 455/410 |
| 10,226,187 B2 * | 3/2019 | Al-Ali | A61B 5/0004 |
| 12,048,506 B2 * | 7/2024 | Handler | A61B 5/0205 |

FOREIGN PATENT DOCUMENTS

WO    WO-2006047430 A2 *    5/2006    ............ G06F 9/4411

* cited by examiner

*Primary Examiner* — Tho D Ta
(74) *Attorney, Agent, or Firm* — Nolte Lackenbach Siegel

(57) ABSTRACT

A docking interface configured to dock with another device is provided. The docking interface includes an optical link module comprising a transceiver configured to transmit and receive optical signals; a magnetic field sensor element configured to generate an electrical signal in response to a magnetic field impinging thereon; and at least one processor configured to receive the electrical signal, compare a magnitude of the electrical signal to a proximity threshold value to generate a comparison result, and detect a docking event and an undocking event based on the comparison result.

19 Claims, 19 Drawing Sheets

PATIENT PHYSIOLOGICAL MONITOR MOUNTING DETECTION

CROSS-REFERENCE TO RELATED APPLICATIONS

This application is a continuation of and claims the priority of prior U.S. patent application Ser. No. 17/350,512, filed Jun. 17, 2021 claims priority to and the benefit of U.S. Prov. Pat. App. Ser. No. 63/106,640, which was filed on Oct. 28, 2020 for all purposes, including the right of priority, which application is hereby incorporated herein by reference in its entirety for all purposes.

BACKGROUND

Patient monitors are devices that are configured to receive physiological data from another device and either display a patient's physiological data, monitor a patient's physiological data, or both. A patient monitor may be configured to be worn by a patient, may be a hand-held device, may be docked to or undocked from a larger unit such as a monitor mount, and, thus, may be transportable. For example, a monitor mount may be a larger patient monitor or a console that has a docking interface or docking receptacle to which the patient monitor can be removably docked. Once docked, the patient monitor and the monitor mount communicate using optical transmission signals. A photo transceiver that includes a bi-directional diode may be used for such optical communications using, for example, infrared light. Depending on the type of patient monitor or the type of monitor mount, a photo transceiver may be provided at both devices such that bi-directional optical communication is possible or may only be provided at one of the devices such that optical communication is not possible. Typically, the bi-directional diode is always receiving power and thus always on. This includes instances when the patient monitor is not docked or in the process of being docked and instances when either one of either the patient monitor or the monitor mount does not include a photo transceiver. Being always turned on diminishes the lifetime of the bi-directional diode and may lead to early failure.

Thus, a system that regulates the power to the bi-directional diode based on a docking or mounting event to preserve the life thereof may be desirable.

SUMMARY

One or more embodiments provide a docking interface configured to dock with another device, including: an optical link module including a transceiver configured to transmit and receive optical signals; a magnetic field sensor element configured to generate an electrical signal in response to a magnetic field impinging thereon; and at least one processor configured to receive the electrical signal, compare a magnitude of the electrical signal to a proximity threshold value to generate a comparison result, and detect a docking event and an undocking event based on the comparison result.

One or more embodiments provide a docking interface configured to dock with another device, including: a power supply; a power contact configured to be selectively connected and disconnected to the power supply; a magnetic field sensor element configured to generate an electrical signal in response to a magnetic field impinging thereon; at least one processor configured to receive the electrical signal, compare a magnitude of the electrical signal to a proximity threshold value to generate a comparison result, and detect a docking event and an undocking event based on the comparison result, wherein the at least one processor is configured to connect the power contact to the power supply in response to detecting the docking event to enable power to be distributed to the other device, and wherein the at least one processor is configured to disconnect the power contact from the power supply in response to detecting the undocking event.

One or more embodiments provide a docking interface configured to dock with another device, including: a rechargeable power supply; a power contact configured to be selectively connected and disconnected to the rechargeable power supply; a power distribution controller configured to monitor a value of a power signal received at the power contact, including comparing the value to a threshold value to generate a comparison result and determining whether or not the docking interface is fully docked with the other device based on the comparison result, wherein, in response to the value being equal or greater than the threshold value, the power distribution controller is further configured to connect the power contact to the rechargeable power supply to enable power to be distributed from the other device to the rechargeable power supply via the power contact to recharge the rechargeable power supply, and wherein, in response to the value being less than the threshold value, the power distribution controller is further configured to disconnect the power contact from the rechargeable power supply.

One or more embodiments provide a docking interface configured to dock with another device, including: a rechargeable power supply; a power contact configured to be selectively connected and disconnected to the rechargeable power supply; a docked signal contact configured to receive a docked signal from the other device indicating that the docking interface is fully docked with the other device; and at least one processor configured to selectively connect and disconnect the power contact to the rechargeable power supply based on detecting the docked signal, wherein, in response to detecting the docked signal, the at least one processor is configured to connect the power contact to the rechargeable power supply to enable power to be distributed from the other device to the rechargeable power supply via the power contact to recharge the rechargeable power supply, and wherein, in response to not detecting the docked signal, the at least one processor is configured to disconnect the power contact from the rechargeable power supply.

One or more embodiments provide a method of docking a docking interface with another device, the method including: a magnetic field sensor element configured to generate an electrical signal in response to a magnetic field impinging thereon; at least one processor configured to receive the electrical signal, compare a magnitude of the electrical signal to a proximity threshold value to generate a comparison result, and detect a docking event and an undocking event based on the comparison result; in response to detecting the docking event when the magnitude of the electrical signal is greater than the proximity threshold value, enabling a transceiver to transmit optical signals, in response to enabling the transceiver during the docking event, monitoring for reflected optical signals corresponding to the transmitted optical signals, the reflected optical signals being received at the transceiver; and in response to detecting a number of one or more reflected optical signals during the docking event, disabling the transceiver.

One or more embodiments provide a method of docking a docking interface with another device, the method including: generating, by a magnetic field sensor element integrated at the docking interface, an electrical signal in response to a magnetic field impinging thereon; at least one processor configured to receive the electrical signal, compare a magnitude of the electrical signal to a proximity threshold value to generate a comparison result, and detect a docking event and an undocking event based on the comparison result; and selectively connecting and disconnecting a power contact integrated at the docking interface with a power supply based on detecting the docking event and an undocking event, including connecting the power contact to the power supply, wherein the power contact is connected to the power supply in response to detecting the docking event to enable power to be distributed to the other device, and wherein the power contact is disconnected from the power supply in response to detecting the undocking event.

One or more embodiments provide a method of docking a docking interface with another device, the method including: monitoring a value of a power signal received at a power contact that is integrated at the docking interface, including comparing the value to a threshold value to generate a comparison result and determining whether or not the docking interface is fully docked with the other device based on the comparison result; in response to the value being equal or greater than the threshold value, connect the power contact to a rechargeable power supply to enable power to be distributed from the other device to the rechargeable power supply via the power contact to recharge the rechargeable power supply; and in response to the value being less than the threshold value, disconnecting the power contact from the rechargeable power supply.

BRIEF DESCRIPTION OF THE DRAWINGS

In the drawings, like reference numbers generally indicate identical, functionally similar, and/or structurally similar elements.

DETAILED DESCRIPTION

Figure 1:
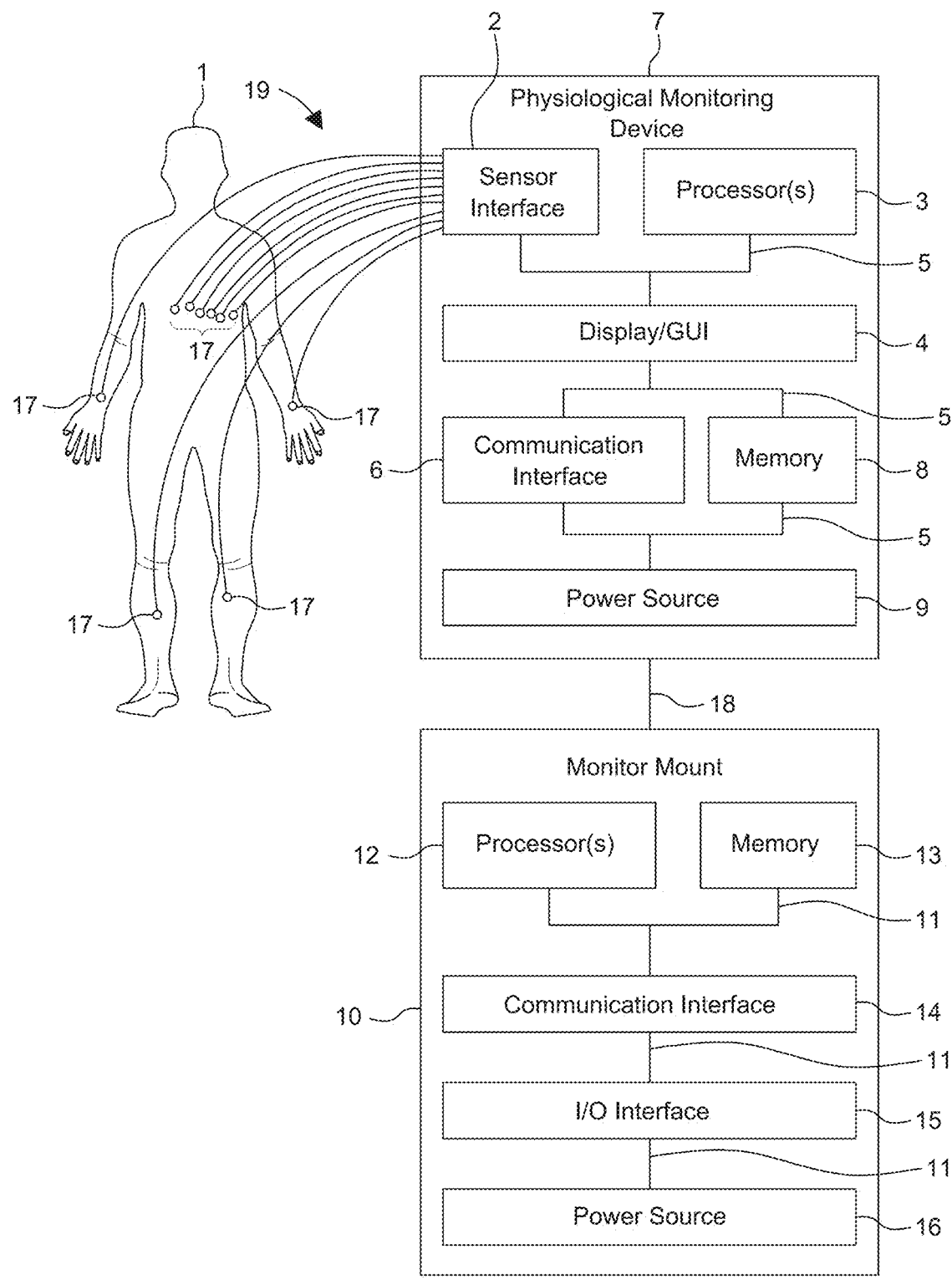
FIG. 1 shows a physiological monitoring system according to one or more embodiments.

In the following, details are set forth to provide a more thorough explanation of the embodiments. However, it will be apparent to those skilled in the art that embodiments may be practiced without these specific details. In other instances, well-known structures and devices are shown in block diagram form or in a schematic view rather than in detail in order to avoid obscuring the embodiments. In addition, features of the different embodiments described hereinafter may be combined with each other, unless specifically noted otherwise. For example, variations or modifications described with respect to one of the embodiments may also be applicable to other embodiments unless noted to the contrary.

Further, equivalent or like elements or elements with equivalent or like functionality are denoted in the following description with equivalent or like reference numerals. As the same or functionally equivalent elements are given the same reference numbers in the figures, a repeated description for elements provided with the same reference numbers may be omitted. Hence, descriptions provided for elements having the same or like reference numbers are mutually exchangeable.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

In the present disclosure, expressions including ordinal numbers, such as "first", "second", and/or the like, may modify various elements. However, such elements are not limited by the above expressions. For example, the above expressions do not limit the sequence and/or importance of the elements. The above expressions are used merely for the purpose of distinguishing an element from the other elements. For example, a first box and a second box indicate different boxes, although both are boxes. For further example, a first element could be termed a second element, and similarly, a second element could also be termed a first element without departing from the scope of the present disclosure.

Directional terminology, such as "top", "bottom", "below", "above", "front", "behind", "back", "leading", "trailing", etc., may be used with reference to the orientation of the figures being described. Because parts of embodiments can be positioned in a number of different orientations, the directional terminology is used for purposes of illustration. It is to be understood that other embodiments may be utilized, and structural or logical changes may be made without departing from the scope defined by the claims. The following detailed description, therefore, is not to be taken in a limiting sense. Directional terminology used in the claims may aid in defining one element's spatial or positional relation to another element or feature, without being limited to a specific orientation.

Instructions may be executed by one or more processors, such as one or more central processing units (CPU), digital signal processors (DSPs), general purpose microprocessors, application specific integrated circuits (ASICs), field programmable logic arrays (FPGAs), or other equivalent integrated or discrete logic circuitry. Accordingly, the term "processor," as used herein refers to any of the foregoing structure or any other structure suitable for implementation of the techniques described herein. In addition, in some aspects, the functionality described herein may be provided within dedicated hardware and/or software modules. Also, the techniques could be fully implemented in one or more circuits or logic elements. A "controller," including one or more processors, may use electrical signals and digital algorithms to perform its receptive, analytic, and control functions, which may further include corrective functions. Thus, a controller is a specific type of processing circuitry, comprising one or more processors and memory, that implements control functions by way of generating control signals.

A sensor refers to a component which converts a physical quantity to be measured to an electric signal, for example, a current signal or a voltage signal. The physical quantity may for example comprise electromagnetic radiation (e.g., photons of infrared or visible light), a magnetic field, an electric field, a pressure, a force, a temperature, a current, or a voltage, but is not limited thereto. A magnetic field sensor, for example, includes one or more magnetic field sensor elements that measure one or more characteristics of a magnetic field (e.g., an amount of magnetic field flux density, a field strength, a field angle, a field direction, a field orientation, etc.). In the embodiments that follow, the magnetic field is produced by one or more magnets. However, a current-carrying conductor (e.g., a wire) also generates a magnetic field and can also be a magnetic field source. Each magnetic field sensor element is configured to generate a sensor signal (e.g., a voltage signal) in response to one or more magnetic fields impinging on the sensor element. Thus, a sensor signal is indicative of the magnitude and/or the orientation of the magnetic field impinging on the sensor element.

Magnetic field sensor elements include magnetoresistive sensor elements, inductive sensor elements, and Hall-effect sensor elements (Hall sensor elements), for example, and are mutually exchangeable in the embodiments provided herein. According to one or more embodiments, a plurality of magnetic field sensor elements and a sensor circuitry may be both accommodated (i.e., integrated) in the same chip. The sensor circuit may be referred to as a signal processing circuit and/or a signal conditioning circuit that receives one or more signals (i.e., sensor signals) from one or more magnetic field sensor elements in the form of raw measurement data and derives, from the sensor signal, a measurement signal or sensor data that represents the magnetic field and/or the detection thereof.

Signal conditioning, as used herein, refers to manipulating an analog signal in such a way that the signal meets the requirements of a next stage for further processing. Signal conditioning may include converting from analog to digital (e.g., via an analog-to-digital converter), amplification, filtering, converting, biasing, range matching, isolation and any other processes required to make a sensor output suitable for processing after conditioning.

Thus, the sensor circuit may include an analog-to-digital converter (ADC) that converts the analog signal from the one or more sensor elements to a digital signal. The sensor circuit may also include a DSP that performs some processing on the digital signal, to be discussed below. Therefore, a chip, which may also be referred to as an integrated circuit (IC), may include a circuit that conditions and amplifies the small signal of one or more magnetic field sensor elements via signal processing and/or conditioning.

FIG. 1 shows a physiological monitoring system according to one or more embodiments. As shown in FIG. 1, the system includes a patient monitor 7 (i.e., a physiological monitoring device (PMD)) capable of receiving physiological data from various sensors 17 connected to a patient 1, and a monitor mount 10 to which the patient monitor 7 is removably mounted or docked.

In general, it is contemplated by the present disclosure that the patient monitor 7 and the monitor mount 10 include electronic components and/or electronic computing devices operable to receive, transmit, process, store, and/or manage patient data and information associated performing the functions of the system, which encompasses any suitable processing device adapted to perform computing tasks consistent with the execution of computer-readable instructions stored in a memory or a computer-readable recording medium.

Further, any, all, or some of the computing devices in the patient monitor 7 and the monitor mount 10 may be adapted to execute any operating system, including Linux, UNIX, Windows Server, etc., as well as virtual machines adapted to virtualize execution of a particular operating system, including customized and proprietary operating systems. The patient monitor 7 and the monitor mount 10 are further equipped with components to facilitate communication with other computing devices over one or more network connections, which may include connections to local and wide area networks, wireless and wired networks, public and private networks, and any other communication network enabling communication in the system.

As shown in FIG. 1, the patient monitor 7 is, for example, a patient monitor implemented to monitor various physiological parameters of the patient 1 via the sensors 17. The patient monitor 7 includes a sensor interface 2, one or more processors 3, a display/GUI 4, a communications interface 6, a memory 8, and a power source 9. The sensor interface 2 can be implemented in hardware or combination of hardware and software and is used to connect via wired and/or wireless connections 19 to one or more sensors 17 for gathering physiological data from the patient 1. The sensors 17 may be physiological sensors and/or medical devices configured to measure one or more of the physiological parameters and output the measurements via a corresponding one or more connections 19 to the sensor interface 2. Thus, the connections 19 represent one or more wired or wireless communication channels configured to at least transmit sensor data from a corresponding sensor 17 to the sensor interface 2.

By way of example, sensors 17 may include electrodes that attach to the patient for reading electrical signals generated by or passed through the patient 1. Sensors 17 may be configured to measure vital signs, measure electrical stimulation, measure brain electrical activity such as in the case of a electroencephalogram (EEG), measure blood oxygen saturation fraction from absorption of light at different wavelengths as it passes through a finger, measure a CO2 level and/or other gas levels in an exhalation stream using infrared spectroscopy, measure oxygen saturation on the surface of the brain or other regions, measure cardiac output from invasive blood pressure and temperature measurements, measure induced electrical potentials over the cortex of the brain, measure blood oxygen saturation from an optical sensor coupled by fiber to the tip of a catheter, and/or measure blood characteristics using absorption of light.

The data signals from the sensors 17 include, for example, sensor data related to an electrocardiogram (ECG), non-invasive peripheral oxygen saturation (SpO2), non-invasive blood pressure (NIBP), body temperature, tidal carbon dioxide (etCO2), apnea detection, and/or other physiological data, including those described herein. The one or more processors 3 are used for controlling the general operations of the patient monitor 7, as well as processing sensor data received by the sensor interface 2. Each one of the one or more processors 3 can be, but are not limited to, a central processing unit (CPU), a hardware microprocessor, a multi-core processor, a single core processor, a field programmable gate array (FPGA), a microcontroller, an application specific integrated circuit (ASIC), a digital signal processor (DSP), or other similar processing device capable of executing any type of instructions, algorithms, or software for controlling the operation and performing the functions of the patient monitor 7.

The display/GUI 4 is configured to display various patient data, sensor data, and hospital or patient care information, and includes a user interface implemented for allowing interaction and communication between a user and the patient monitor 7. The display/GUI 4 includes, but is not limited to, a keyboard, a liquid crystal display (LCD), cathode ray tube (CRT) display, thin film transistor (TFT) display, light-emitting diode (LED) display, high definition (HD) display, or other similar display device that may include touch screen capabilities. The display/GUI 4 also provides a means for inputting instructions or information directly to the patient monitor 7. The patient information displayed can, for example, relate to the measured physiological parameters of the patient 1 (e.g., blood pressure, heart related information, pulse oximetry, respiration information, etc.) as well as information related to the transporting of the patient 1 (e.g., transport indicators).

The communications interface 6 enables the patient monitor 7 to directly or indirectly (via, for example, the monitor mount 10) communicate with one or more computing networks and devices, including one or more sensors 17, workstations, consoles, computers, monitoring equipment, alert systems, and/or mobile devices (e.g., a mobile phone, tablet, or other hand-held display device). The communications interface 6 can include various network cards, interfaces, communication channels, cloud, antennas, and/or circuitry to enable wired and wireless communications with such computing networks and devices. The communications interface 6 can be used to implement, for example, a Bluetooth connection, a cellular network connection, and/or a Wi-Fi connection with such computing networks and devices. Example wireless communication connections implemented using the communications interface 6 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

Additionally, the communications interface 6 can enable direct (i.e., device-to-device) communications (e.g., messaging, signal exchange, etc.) such as from the monitor mount 10 to the patient monitor 7 using, for example, a universal serial bus (USB) connection or other communication protocol interface. The communications interface 6 can also enable direct device-to-device connection to other device such as to a tablet, computer, or similar electronic device; or to an external storage device or memory.

The memory 8 can be a single memory device or one or more memory devices at one or more memory locations that include, but is not limited to, a random access memory (RAM), a memory buffer, a hard drive, a database, an erasable programmable read only memory (EPROM), an electrically erasable programmable read only memory (EEPROM), a read only memory (ROM), a flash memory, hard disk, various layers of memory hierarchy, or any other non-transitory computer readable medium. The memory 8 can be used to store any type of instructions and patient data associated with algorithms, processes, or operations for controlling the general functions and operations of the patient monitor 7.

The power source 9 can include a self-contained power source such as a battery pack and/or include an interface to be powered through an electrical outlet (either directly or by way of the monitor mount 10). The power source 9 can also be a rechargeable battery that can be detached allowing for replacement. In the case of a rechargeable battery, a small built-in back-up battery (or super capacitor) can be provided for continuous power to be provided to the patient monitor 7 during battery replacement. Communication between the components of the patient monitor 7 (e.g., components 2, 3, 4, 6, 8, and 9) are established using an internal bus 5.

Accordingly, the patient monitor 7 is attached to one or more of several different types of sensors 17 configured to measure and readout physiological data related to the patient 1 (e.g., as shown on the left side of FIG. 1). One or more sensors 17 may be attached to patient monitor 7 by, for example, a wired connection coupled to the sensor interface 2. Additionally, or alternatively, one or more sensors 17 may be a wireless sensor that is communicatively coupled to the patient monitor 7 via the communication interface 6, which includes circuitry for receiving data from and sending data to one or more devices using, for example, a Wi-Fi connection, a cellular network connection, and/or a Bluetooth connection.

The data signals from the sensors 17 received by the patient monitor 7 may include sensor data related to, for example, body temperature (BT), pulse (heart rate (HR)), and breathing rate (respiratory rate) (RR), an ECG, SpO2, NIBP, and/or etCO2.

The data signals received from the sensors, including an ECG sensor and an SpO2 sensor, can be analog signals. For example, the data signals for the ECG and the SpO2 are input to the sensor interface 2, which can include an ECG data acquisition circuit and an SpO2 data acquisition circuit. Both the ECG data acquisition circuit and the SpO2 data acquisition circuit may include amplifying and filtering circuitry as well as analog-to-digital (A/D) circuitry that converts the analog signal to a digital signal using amplification, filtering, and A/D conversion methods. In the event that the ECG sensor and the SpO2 sensor are wireless sensors, the sensor interface 2 may receive the data signals from a wireless commination module. Thus, a sensor interface is a component configured to interface with one or more sensors 17 and receive sensor data therefrom.

As another example, the data signals related to NIBP, body temperature, and etCO2 can be received from sensors 17 to the sensor interface 2, which can include a physiological parameter interface such as serial interface circuitry for receiving and processing the data signals related to NIBP, temperature, and etCO2. In FIG. 1, the ECG data acquisition circuit, an SpO2 data acquisition circuit, and physiological parameter interface are described as part of the sensor interface 2. However, it is contemplated by the present disclosure that the ECG data acquisition circuit, the SpO2 data acquisition circuit, and physiological parameter interface can be implemented as circuits separate from the sensor interface 2. In the event that the NIBP sensor, the temperature sensor, and the etCO2 sensor are wireless sensors, the sensor interface 2 may receive the data signals from a wireless commination module.

The processing performed by the ECG data acquisition circuit, the SpO2 data acquisition circuit, and external physiological parameter interface may generate analog data waveforms or digital data waveforms that are analyzed by a microcontroller. The microcontroller may be one of the processors 3. The microcontroller, for example, analyzes the digital waveforms to identify certain digital waveform characteristics and threshold levels indicative of conditions (abnormal and normal) of the patient 1 using one or more monitoring methods. A monitoring method may include comparing an analog or a digital waveform characteristic or an analog or digital value to one or more threshold values and generating a comparison result based thereon. The microcontroller is, for example, a processor, an FPGA, an ASIC, a DSP, a microcontroller, or similar processing device. The microcontroller includes a memory or uses a separate memory 8. The memory is, for example, a RAM, a memory buffer, a hard drive, a database, an EPROM, an EEPROM, a ROM, a flash memory, a hard disk, or any other non-transitory computer readable medium.

The memory stores software or algorithms with executable instructions and the microcontroller can execute a set of instructions of the software or algorithms in association with executing different operations and functions of the patient monitor 7 such as analyzing the digital data waveforms related to the data signals from the sensors 17.

As shown in FIG. 1, the patient monitor 7 is connected to the monitor mount 10 via a connection 18 that establishes a communication connection between, for example, the respective communications interfaces 6, 14 of the devices 7, 10. The connection 18 is an interface that enables the monitor mount 10 to detachably secure the patient monitor 7 to the monitor mount 10. In this regard, "detachably secure" means that the monitor mount 10 can receive and secure the patient monitor 7, but the patient monitor 7 can also be removed or undocked from the monitor mount 10 by a user when desired. In other words, the patient monitor 7 can be removably docked or removably mounted to the monitor mount 10 and the connection 18 forms an electrical and/or optical connection between the devices 7, 10 for enabling communication therebetween. In this way, the monitor mount 10 may include a mounting or docking receptacle for receiving the patient monitor 7 therein as part of its mounting or docking interface.

The connection 18 may also enable the transmission of power from the monitor mount 10 to the patient monitor 7 for charging the power source 9. The connection 18 may also enable the patient monitor 7 to detect whether it is in a docked or undocked state. Thus, the connection 18 may further enable the patient monitor 7 and/or the monitor mount 10 via the interface to detect an undocking event and a docking event by detecting a proximity, or an absence thereof, between the patient monitor 7 and the monitor mount 10.

The connection 18 may include, but is not limited to, a USB connection, a parallel connection, a serial connection, a coaxial connection, a High-Definition Multimedia Interface (HDMI) connection, an optical connection, and/or any other electrical connection configured to connect electronic devices and transmit data and/or power therebetween.

The monitor mount 10 includes one or more processors 12, a memory 13, a communications interface 14, an I/O interface 15, and a power source 16. The one or more processors 12 are used for controlling the general operations of the monitor mount 10 and may be further used to controller one or more operations of the patient monitor 7 when mounted to the monitor mount 10. Each one of the one or more processors 12 can be, but are not limited to, a CPU, a hardware microprocessor, a multi-core processor, a single core processor, an FPGA, a microcontroller, an ASIC, a DSP, or other similar processing device capable of executing any type of instructions, algorithms, or software for controlling the operation and performing the functions of the monitor mount 10.

The memory 13 can be a single memory or one or more memories or memory locations that include, but are not limited to a RAM, a memory buffer, a hard drive, a database, an EPROM, an EEPROM, a ROM, a flash memory, hard disk, or various layers of memory hierarchy, or any other non-transitory computer readable medium. The memory 13 can be used to store any type of instructions associated with algorithms, processes, or operations for controlling the general functions and operations of the monitor mount 10.

The communications interface 14 allows the monitor mount 10 to communicate with one or more computing networks and devices (e.g., the patient monitor 7, workstations, consoles, computers, monitoring equipment, alert systems, and/or mobile devices (e.g., a mobile phone, tablet, or other hand-held display device). The communications interface 14 can include various network cards, interfaces, communication channels, antennas, and/or circuitry to enable wired and wireless communications with such computing networks and devices. The communications interface 14 can also be used to implement, for example, a Bluetooth connection, a cellular network connection, cloud-based connection, and a Wi-Fi connection. Example wireless communication connections implemented using the communications interface 14 include wireless connections that operate in accordance with, but are not limited to, IEEE802.11 protocol, a Radio Frequency For Consumer Electronics (RF4CE) protocol, and/or IEEE802.15.4 protocol (e.g., ZigBee protocol). In essence, any wireless communication protocol may be used.

The communications interface 14 can also enable direct (i.e., device-to-device) communications (e.g., messaging, signal exchange, etc.) such as from the monitor mount 10 to the patient monitor 7 or vice versa using, for example, the connection 18. The communications interface 14 can enable direct (i.e., device-to-device) to other device such as to a tablet, PC, or similar electronic device; or to an external storage device or memory.

The I/O interface 15 can be an interface for enabling the transfer of information between monitor mount 10, one or more patient monitors 7, and external devices such as peripherals connected to the monitor mount 10 that need special communication links for interfacing with the one or more processors 12. The I/O interface 15 can be implemented to accommodate various connections to the monitor mount 10 that include, but is not limited to, a USB connection, a parallel connection, a serial connection, a coaxial connection, an HDMI connection, or any other electrical connection configured to connect electronic devices and transmit data therebetween.

The power source 16 can include a self-contained power source such as a battery pack and/or include an interface to be powered through an electrical outlet (either directly or by way of the patient monitor 7). The power source 16 can also be a rechargeable battery that can be detached allowing for replacement. Communication between the components of the monitor mount 10 (e.g., components 12, 13, 14, 15 and 16) are established using an internal bus 11.

Figure 2A:
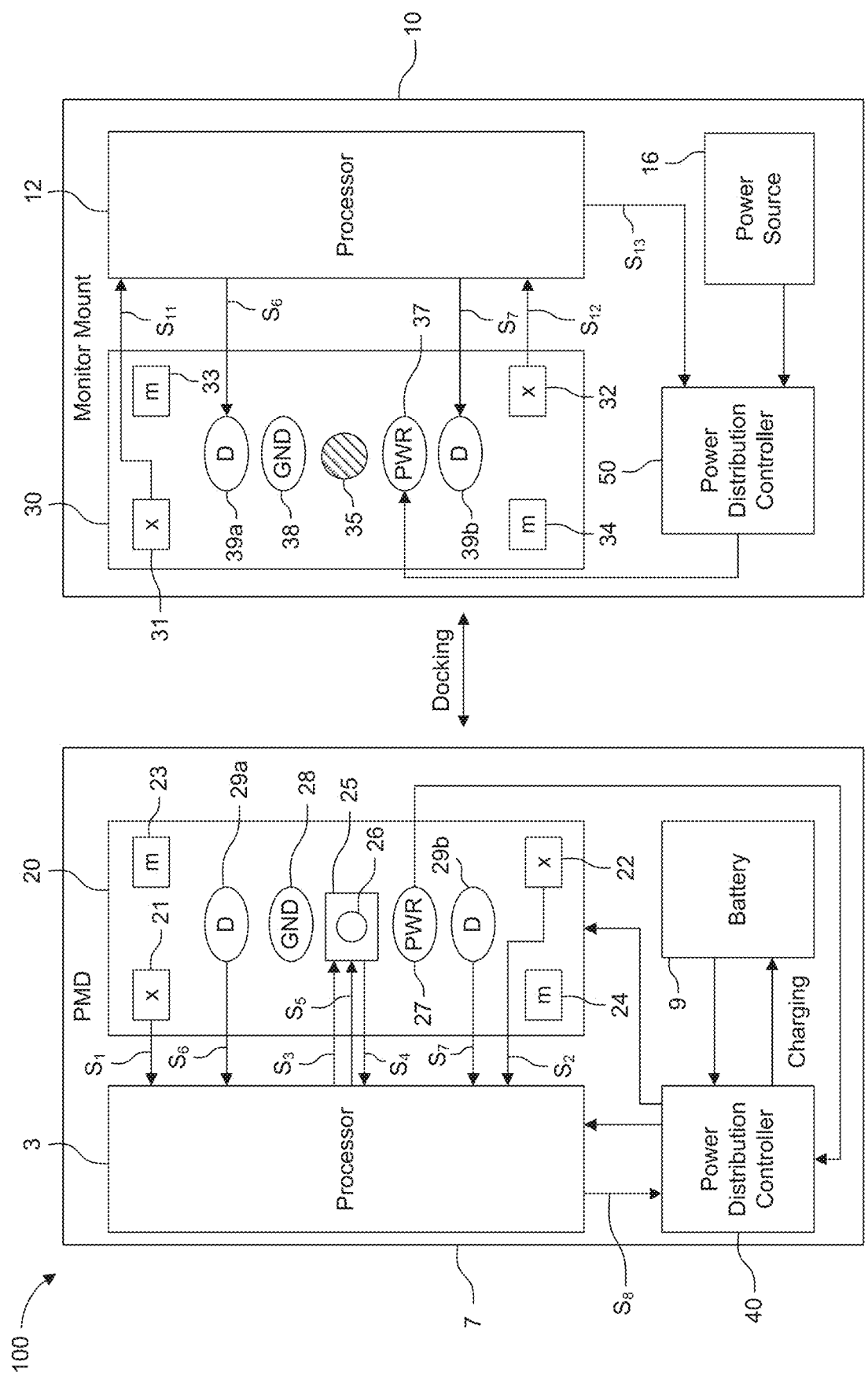
FIG. 2A is a schematic block diagram of a docking system 100 according to one or more embodiments.

FIG. 2A is a schematic block diagram of a docking system 100 according to one or more embodiments. The docking system 100 is for docking the patient monitor 7 to the monitoring mount 10 and undocking the patient monitor 7 from the monitoring mount 10. In particular, the patient monitor 7 includes a docking interface 20 and the monitoring mount 10 includes a docking interface 30 whose elements are arranged in a corresponding interfacing relationship or a reciprocating docking configuration to the elements of the docking interface 20 when the two interfaces 20 and 30 are docked together. In other words, the elements on the two interfaces 20 and 30 mirror each other so that when one interface is placed in proximity of the other that the corresponding elements are in alignment.

Both the patient monitor 7 and the monitoring mount 10 include additional circuitry for processing signals and/or performing control functions based on stored algorithms. In particular, the patient monitor 7 includes at least one processor 3, a power source 9 (i.e., a rechargeable battery), and a charge controller 40. The power source 9 is electrically coupled to the power distribution controller 40, the processor 3 via the power distribution controller 40, and the docking interface 20 via the power distribution controller 40 for supplying power thereto, including to individual elements thereof, while the patient monitor 7 is undocked from an alternate power source (e.g., power source 16). The monitoring mount 10 includes at least one processor 12, a power source 16, and a power distribution controller 50. The power source 16 provides power to the elements at the monitoring mount 10 that require power, as well as provides power to the patient monitor 7 via the power distribution controller 50 when the patient monitor 7 is docked at the monitoring mount 10. Specifically, the power source 9 of the patient monitor 7 receives power from power source 16 while docked for recharging.

The docking interface 20 includes magnetic field sensor elements 21 and 22 that generate sensor signals S1 and S2 corresponding to a measured magnetic field and provide the sensor signals to the processor 3 for processing. The processor 3 is configured to compare the value (e.g., magnitude) of the sensor signals to a proximity threshold value and provide further action based on the comparison result. The docking interface 20 further includes magnets 23 and 24 that produce a magnetic field used by docking interface 30 for proximity detection. The docking interface 20 further includes an optical link module (OLM) 25. The docking interface 20 further includes various contacts, including a power (PWR) contact 27 coupled to the power distribution controller 40 for providing power received from power source 16 thereto, a ground (GND) contact 28 configured to be connected to circuit ground, and one or more docked (D) signal contacts 29a and 29b that are configured to receive docked signals S6 and S7 from the monitoring mount 10 that indicates that the patient monitor 7 is fully engaged with the monitor mount 10 and that docking is fully complete. The docked signals S6 and S7 may be a voltage or current generated by a corresponding docked (D) signal contact (e.g., contacts 39a and 39b) at the monitor mount 10.

The OLM 25 is a bi-directional phototransceiver that includes an optical transmitter and an optical receiver, such as a bi-directional diode 26. The bi-directional diode 26 is configured to transmit infrared light (optical transmission signals) based on trigger signals received from circuitry of the bi-directional phototransceiver. The processor 3 may provide communication data to the OLM 25 via data signal S3 and the OLM 25 is configured to transmit the communication data by way of the optical transmission signals (e.g., into free space towards interface 30) in accordance with the data signal S3.

In addition, the bi-directional diode 26 is configured to receive infrared light. The received infrared light may be optical receive signals received from another OLM arranged along a communication path of the OLM 25 or may be reflected transmission signals that were transmitted by the bi-directional diode 26 and subsequently reflected by a reflective structure (e.g., a mirror, reflective disk, or the like) that is arranged along the communication path of the OLM 25. Aluminum used as a reflective surface has good reflectivity for infrared wavelengths. However, other types of reflective materials can be used.

The bi-directional diode 26 is configured to generate electrical signals S4 based on the received light and provide the electrical signals S4 to the processor 3 for processing, including decoding. More particularly, in response to receiving infrared light, the bi-directional diode 26 generates electrical signals representative of the received infrared light and provides the electrical signals to the circuitry of the OLM 25 that subsequently transmits the electrical signals to the processor 3. The processor 3 is configured to decode the electrical signals to determine whether the received infrared light originated from another OLM corresponding to optical receive signals or from its own OLM 25 corresponding to reflected transmission signals.

The processor 3 may be configured to make a correlation when it receives its own transmission signals. For example, optical signals may be encoded via frequency modulation or amplitude modulation. A packet header may be encoded into the optical signal with a unique identifier corresponding to the OLM 25. The processor 3 can identify the optical signal as a reflected transmission signal when the extracted identifier matches the unique identifier of the OLM 25.

In a specific example, the Address Resolution Protocol (ARP) may be used. Here, the OLM 25 is configured to transmit ARP packets that include its own identifying information (e.g., a sender hardware address (SHA)). The processor 3 is configured to recognize a received transmission as a reflected transmission signal when its address information matches the address information received in the received signal. Other means of identifying received transmission signals as reflected transmission signals are also possible. If the processor 3 determines that its address information does not match the address information received in the received signal, the processor 3 determines that the signal originated from another device (e.g., another OLM) and proceeds to establish an optical communication link with the other device.

As will be discussed in further detail below, the processor 3 is configured to count the number of consecutive reflected transmission signals for detecting a docking event between the patient monitor 7 and the monitor mount 10.

The processor 3 is further configured to transmit control signals S5 to the OLM 25 for enabling or disabling the bi-directional diode 26. Thus, upon receipt of an enable control signal, the OLM 25 enables (e.g., powers on) the bi-directional diode 26 such that optical transmissions are possible. Conversely, upon receipt of a disable control signal, the OLM 25 disables (e.g., powers off) the bi-directional diode 26 such that optical transmissions are not possible.

The docking interface 30 includes magnetic field sensor elements 31 and 32 that generate sensor signals corresponding to a measured magnetic field and provide the sensor signals to the processor 12 for processing. The magnetic field sensor elements 31 and 32 are arranged in an interfacing relationship to magnets 23 and 24, respectively, of the patient monitor 7. Thus, in a docking maneuver during which the patient monitor 7 is being docked with the monitor mount 10, the magnitude of the sensor signals S11 and S12 increase as interface 20 is brought closer to interface 30 (i.e., as the sensor elements 31 and 32 are brought closer to magnets 23 and 24). The processor 12 is configured to compare the value (e.g., magnitude) of the sensor signals S11 and S12 to a proximity threshold value and provide further action based on the comparison result.

The docking interface 30 further includes magnets 33 and 34 that produce a magnetic field used by docking interface 20 for proximity detection. The magnets 33 and 34 are arranged in an interfacing relationship to magnetic field sensor elements 21 and 22, respectively, of the patient monitor 7. Thus, in a docking maneuver during which the patient monitor 7 is being docked with the monitor mount 10, the magnitude of the sensor signals S1 and S2 increase as interface 20 is brought closer to interface 30 (i.e., as the sensor elements 21 and 22 are brought closer to magnets 33 and 34). As noted above, the processor 3 is configured to compare the value (e.g., magnitude) of the sensor signals S1 and S2 to a proximity threshold value and provide further action based on the comparison result.

The docking interface 30 further includes a reflective structure 35 arranged in an interfacing relationship to the OLM 25. More particularly, the reflective structure 35 is arranged along the communication path of the OLM 25 during a docking maneuver. Thus, as the patient monitor 7 is moved into position to be docked with the monitor mount 10, the communication path of the OLM 25 is aligned with the reflective structure 35. As a result, optical signals transmitted by the bi-directional diode 26 during docking are reflected back at the bi-directional diode 26 as reflected transmission signals. The processor 3 is configured to count the number of consecutive reflected transmission signals received at the bi-directional diode 26 for detecting a docking event between the patient monitor 7 and the monitor mount 10. The processor 3 performs this counting function to confirm that a docking maneuver is being performed and to prevent out a false docking detection. For example, the OLM 25 may transmit an optical signal that is reflected back unintentionally by another object or by the reflective structure 35 when a docking maneuverer is not intended. By requiring a certain number of consecutive reflected transmission signals to be received at the bi-directional diode 26 before a docking event is detected, the processor 3 ensures that the docking maneuver is intended.

The docking interface 30 further includes various contacts that are in corresponding alignment with the various contacts of the docking interface 30. The various contacts of docking interface 30 include a power (PWR) contact 37 coupled to the power distribution controller 50 for providing power received from power source 16 to power source 9 via power contact 27, a ground (GND) contact 38 connected to circuit ground of the monitor mount 10 (not illustrated), and one or more docked (D) signal contacts 39a and 39b that are configured to transmit docked signals S6 and S7 to the patient monitor 7 via docked signal contacts 29a and 29b. Contact made between contacts 29a and 39a and between contacts 29b and 39b allow the transmission of docked signals S6 and S7 to the patient monitor 7 for indicating that the patient monitor 7 is fully engaged with the monitor mount 10 and that docking is fully complete. The docked signals S6 and S7 are received by the docked signal contacts 29a and 29b and passed along to the processor 3.

It will also be appreciated that while two pairs are docked signal contacts are provided, that a signal pair (e.g., 29a/39a or 29b/39b) may be sufficient for detecting docking completion. However, two pairs allows for detection of docking in two opposite docking orientations (inverted orientations). When only one pair is provided (e.g., only contacts 29a and 39a), docking detection is based on whether a single docked signal (e.g., docked signal S6) is present or not. Likewise, it is possible that interface 30 includes only a single magnet 33 or 34. However, two magnets may provide more flexibility in proximity detection during inverted docking orientations between the patient monitor 7 and the monitor mount 10. In a single magnet arrangement, the single magnet may be centrally located in the interface 30 (e.g., adjacent to the mirror structure 35) so that its magnetic field is detectable by at least one of the magnetic field sensors 21 and 22 during a docking maneuver. Thus, a single, centrally located magnet at interface 30 would allow for proximity detection during inverted docking orientations.

Furthermore, the docked signal contacts may also be used to detect a start of an undocking maneuver during which the patient monitor 7 is being separated from the monitor mount 10. For example, if the processor 3 detects that it no longer receives docked signals S6 and/or S7, for example, due to the separation of docked signal contacts 29a and 39a and/or separation of docked signal contacts 29b and 39b, it can determine that an undocking maneuver has begun and take further action.

While some monitor mounts may include its own OLM that enable optical communications with OLM 25, other monitor mounts do not have an OLM. In the case where no linking OLM is present, OLM 25 would still transmit light pulses in search for a link with another OLM with no chance for success. By adding reflective structure 35 to a monitor mount that does not have an OLM for communicating with OLM 25, the patient monitor 7 via processor 3 can detect that optical communications are not needed. Specifically, reflective structure 35 creates reflected transmissions that are reflected back to the patient monitor 7 during a docking maneuver. The reflected transmissions can be used to signal to the processor 3 that optical communications are not needed. As a result, the processor 3 can trigger a shutdown of the bi-directional diode 26 when it is determined that optical transmissions are not needed, thereby preserving the life of the bi-directional diode 26. In addition, when the shutdown of the bi-directional diode 26 is triggered, the processor 3 can further trigger an activation (e.g., a power up) of the wireless communications module of the communications interface 6 to enable wireless communications with the other device.

As the patient monitor 7 approaches the monitor mount 10, proximity detection takes place at both the patient monitor 7 and the monitor mount 10. As the patient monitor 7 approaches the monitor mount 10 for docking, at least one of the magnetic field sensor elements 21 and/or 22 will begin to detect a magnetic field produced by a corresponding one of the magnets 33 and 34. Likewise, at least one of the magnetic field sensor elements 31 and/or 32 will begin to detect a magnetic field produced by a corresponding one of the magnets 23 and 24. In the presence of a magnetic field, a magnetic field sensor element will generate a sensor signal having a magnitude that is proportional both to the strength of the magnetic field produced by the magnet and to a proximity of interface 20 to interface 30. The amplitude of the sensor signal is at its greatest when interface 20 is fully docked at interface 30.

During a docking maneuver, the patient monitor 7 approaches the monitor mount 10 for docking and the magnitude of the sensor signal signals S1, S2, S11, S12 increases. The processors 3 and 12 both include comparators that compare the magnitudes of their received sensor signals a proximity threshold value. The proximity threshold value used by each of the processors 3 and 12 may be the same value or different values.

In response to the magnitude of at least one of sensor signals S1 and S2 becoming equal to or greater than the proximity threshold value, the processor 3 transmits an enable control signal S5 to enable the bi-directional diode 26. While one of the sensor signals S1 and S2 may be sufficient for triggering proximity detection, requiring both to be simultaneously equal to or greater than the proximity threshold value provides a higher confidence that interface 20 is in a docking maneuver with interface 30.

Once enabled, the OLM 25 enables the bi-directional diode 26 to transmit sequential light pulses in search for another OLM to establish a communication link therewith. However, if the processor 3 detects a predetermined number N of reflected transmission signals due to reflections by the reflective structure 35, the processor 3 determines that optical communications are not needed and transmits a disable control signal S5 to the OLM 25 to disable the bi-directional diode 26. Here, N is an integer greater than one. Alternatively, the processor 3 may monitor for a predetermined percentage of reflections where the predetermined percentage may be 80% or greater. In other words, the threshold may be met when 80% of the transmitted light pulses are detected as reflected pulses. Thus, multiple reflected transmission signals should be received before disabling the bi-directional diode 26.

Thus, triggering a reflected transmission event resolves the issue of the bi-directional diode 26 broadcasting signals and diminishing its lifetime even when docked with a monitor mount that does not have an OLM that is in the transmission path of OLM 25. As noted above, the processor 3 is configured to detect and count its own reflected transmission signals. The processor 3 receives electrical signals S4, determines whether each electrical signal S4 corresponds to a reflected transmission signal, and, if so, increments a counter. After receiving a predetermined number of reflected transmission signals N, where N is greater than one, the processor 3 is configured to power down the bi-directional diode 26. This provides a cost effective way to recognize the docking event with the monitor mount 10 and preserves the life of the bi-directional diode 26 for optical communication.

Additionally, processor 3 may disable the bi-directional diode 26 if the magnitude of both sensor signals S1 and S2 falls below the proximity threshold value, indicating that the patient monitor 7 has been pulled away from the monitor mount 10 beyond a predetermined distance corresponding to the proximity threshold value. This may be performed in conjunction with a time out detection where the processor 3 triggers a counter that starts counting up in response to detecting that both sensor signals S1 and S2 fall below the proximity threshold value. If the processor 3 does not detect optical traffic received by the OLM 25 within a predetermined time period based on the counter value, the processor 3 may transmit a disable control signal S5 to the OLM 25 to disable the bi-directional diode 26.

Processor 12 also performs its own proximity detection. In response to the magnitude of at least one of sensor signals S11 and S12 becoming equal to or greater than the proximity threshold value, processor 12 generates docked signals S6 and S7 to enable processor 3 to detect when docking is complete and further generates a power distribution enable signal S13 that instructs the power distribution controller 50 to connect the power source 16 to the power contact 37. By connecting the power source 16 to the power contact 37, the processor 12 allows power (e.g., current) to flow to the power contact 27 when the docking is completed. This ultimately allows for recharging of the power source 9 at the patient monitor 7.

In the event that the magnitudes of both sensor signals S11 and S12 become less than the proximity threshold value indicating, for example, that docking was aborted or that an undocking maneuver is being performed, the processor 12 is configured to send a power distribution disable signal S13 that instructs the power distribution controller 50 to disconnect the power source 16 from the power contact 37. The processor 12 may also cease generating the docked signals S6 and S7 in response to the magnitudes of both sensor signals S11 and S12 becoming less than the proximity threshold value.

When docking is completed, a mechanical latch (not illustrated) holds the patient monitor 7 with a dock of the monitor mount 10. In addition, the processor 3 detects the docked signals S6 and S7 received from the docked signal contacts 29a and 29b. In response to detecting one or both docked signals S6 and S7, the processor 3 transmits a power distribution enable signal S8 to the power distribution controller 40. The power distribution enable signal S8 instructs the power distribution controller 40 to connect the power contact 27 to the power source 9 in order to route the power received at the power contact 27 to the power source 9 for recharging. It may do this by closing a switch that electrically couples the power source 9 to the power contact 27 for receiving power (e.g., current) from the power source 16.

In the event that the processor 3 no longer detects one or both docked signals S6 and S7, the processor 3 may assume that the patient monitor 7 has been separated from the monitor mount 10. In this case, the power distribution controller 40 may transmit a power distribution disable signal S8 to the power distribution controller 40 instructing it to disconnect the power contact 27 from the power source 9, for example, by opening the switch, and thereby ceasing the recharging.

The process also is performed in reverse when an undocking maneuver is performed. As the patient monitor 7 begins to separate from the monitor mount 10, docked signal contacts 29a and 29b are disengaged from docked signal contacts 39a and 39b. The magnetic field sensor elements 21, 22, 31, and 32 are used detect that the patient monitor 7 is no longer within a proximal distance to the monitor mount 10, where the proximal distance is associated with the proximity threshold value.

When the magnitudes of sensor signals S1 and S2 both become less than the proximity threshold value, the processor 3 determines that undocking is complete and transmits an enable control signal S5 to the OLM 25 to enable the bi-directional diode 26. The bi-directional diode 26 then starts to transmit light pulses in search for another OLM to communicate with. During this transmission of light pulses, the processor 3 monitors for optical traffic, including optical transmission signals from another OLM or reflected transmission signals. If the processor 3 detects optical traffic from another OLM within a predetermined time period, an optical link is established between the two OLMs and optical communication continues. If reflected transmission signals are detected, the processor 3 may start the docking process again. On the other hand, if the processor 3 does not detect optical traffic within the predetermined time period, the processor 3 transmits a disable control signal S5 to the OLM 25 to disable the bi-directional diode 26 as optical transmissions are not needed.

Accordingly, the processor 3 may include a counter and a comparator that compares the counter value of the counter to a time period threshold corresponding to the predetermined time period. The counter is started in response to the magnitudes of sensor signals S1 and S2 becoming less than the proximity threshold value after a docking event. The counter is disabled if the controller detects optical traffic within the predetermined time period (i.e., the counter value is less than the time period threshold). The comparator triggers the disable control signal S5 if the processor 3 does not detect optical traffic within the predetermined time period (i.e., the counter value is equal to or greater than the time period threshold).

As noted above, in response to detecting the undocking event, processor 3 disconnects the power source 9 from the power contact 27. This occurs when processor 3 no longer detects the docked signals S6 and S7. In addition, processor 12 disconnects power source 16 from power contact 37. This occurs when processor 12 detects that the magnitudes of sensor signals S11 and S12 have become less than the proximity threshold value. The processor 12 may also cease generation the docked signals S6 and S7 in response to the magnitudes of both sensor signals S11 and S12 becoming less than the proximity threshold value.

Figure 2B:
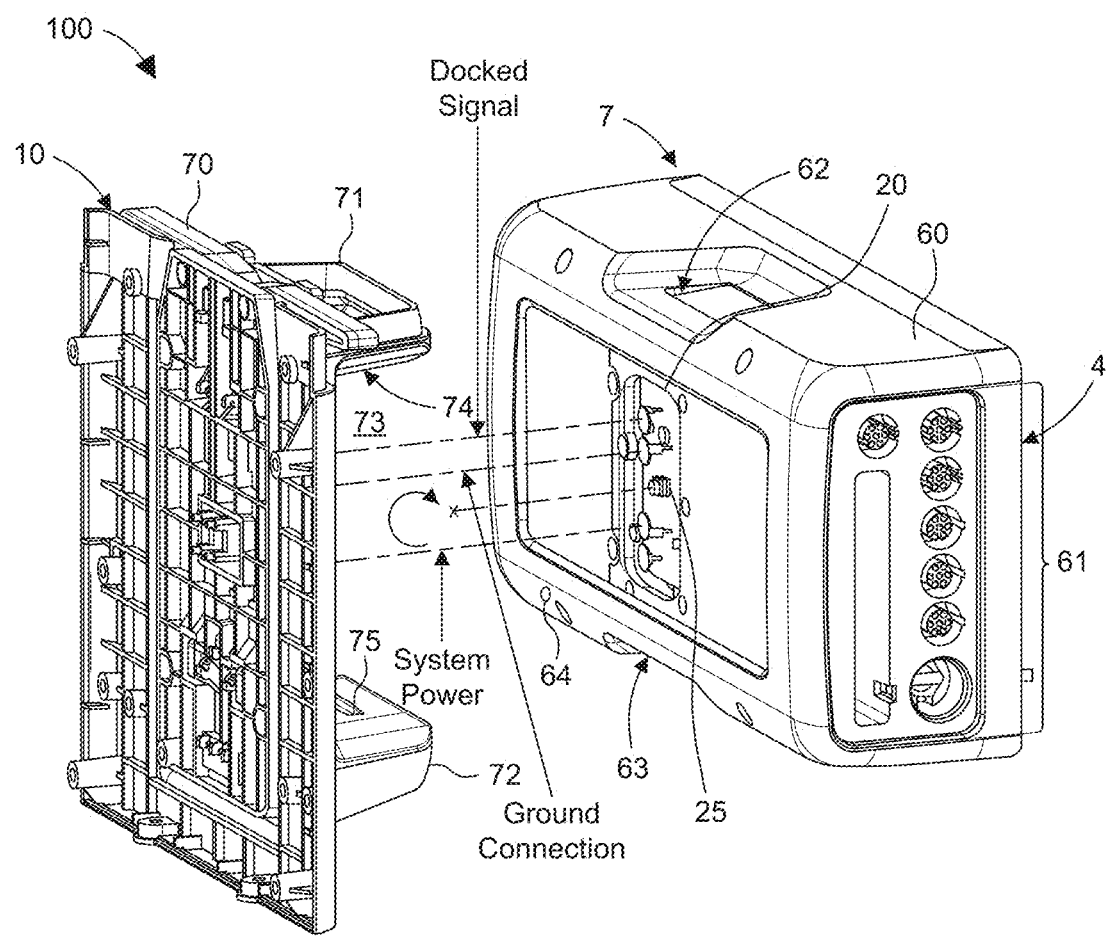
FIGS. 2B and 2C are perspective views of docking system 100 according to one or more embodiments.
Figure 2C:
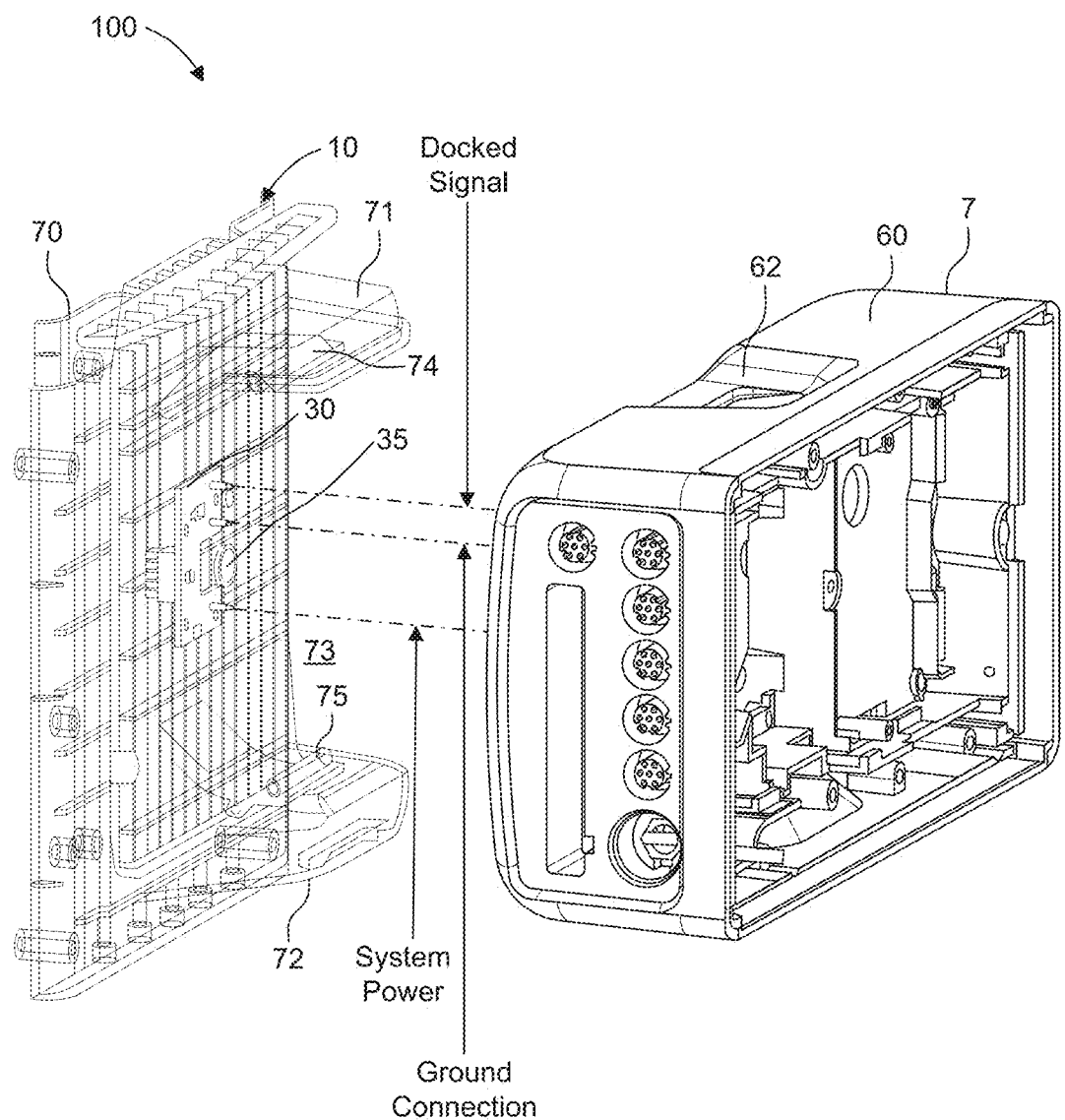

FIGS. 2B and 2C are perspective views of docking system 100 according to one or more embodiments. The patient monitor 7 includes a housing 60 that includes the display 4 at its front face and the docking interface 20 at its rear face. The housing 60 houses the processor 3, the power source 9, and the power distribution controller 40. The housing 60 also includes various connector ports 61 at a side face for being connected to various types of patient monitoring equipment and sensors 17 by wired connections 19. The housing 60 further includes interlocking recesses 62 and 63 located at opposing top and bottom sides of the housing 60 that are each configured to receive a docking arm of the monitor mount 10 for docking. The housing 60 further includes a display port 64 that is configured to receive a display contact (e.g., a pin) from the monitor mount 10.

The monitor mount 10 includes a housing 70 that is configured receive the patient monitor 7 for docking. The housing 70 houses the processor 12, the power source 16, and the power distribution controller 50. The housing 70 includes two docking arms 71 and 72 that extend outward and define a docking recess 73 configured to receive the patient monitor 7 therein. The housing 70 also includes the docking interface 30 on a sidewall interposed between the two docking arms 71 and 72 that is outward facing and configured to engage with interface 20. The two docking arms 71 and 72 each include mechanical latches 74 and 75, respectively, that are configured to interlock with a corresponding interlocking recess 62 or 63 to secure the patient monitor 7 within the docking recess 73.

Due to the reflective element 35 at the interface 30, the light transmitted by the OLM 25 is reflected back towards the bi-directional diode 26 as reflected transmission signals.

It will be appreciated that other types of sensors can be used for detecting docking and undocking events in the alternative to magnetic field sensor elements. For example, accelerometers can be used to sense movement while the patient monitor 7 is in transit. When one device (e.g., patient monitor 7) has an internal accelerometer, the accelerometer is capable of measuring the motion of the device. When there is less motion (the detected motion is lower than a predetermined threshold), it is likely that the monitor is in a static position of being docked. In this case, one or more accelerometers would generate sensor signals having values that exceed a predetermined threshold associated with a motion threshold, followed by steady values once the patient monitor 7 is fully docked to the monitor mount 10. Similarly, an undocking event would follow the opposite progression with the one or more accelerometers generating steady values while docked and generating higher values that exceed the predetermined threshold associated with a motion threshold while being undocked. Radio-frequency identification (RFID) or Near-Field Communication (NFC) sensors could also be used to detect proximity, including a docking maneuver leading up to a docking event and an undocking event performed as a result of an undocking maneuver.

Figure 3A:
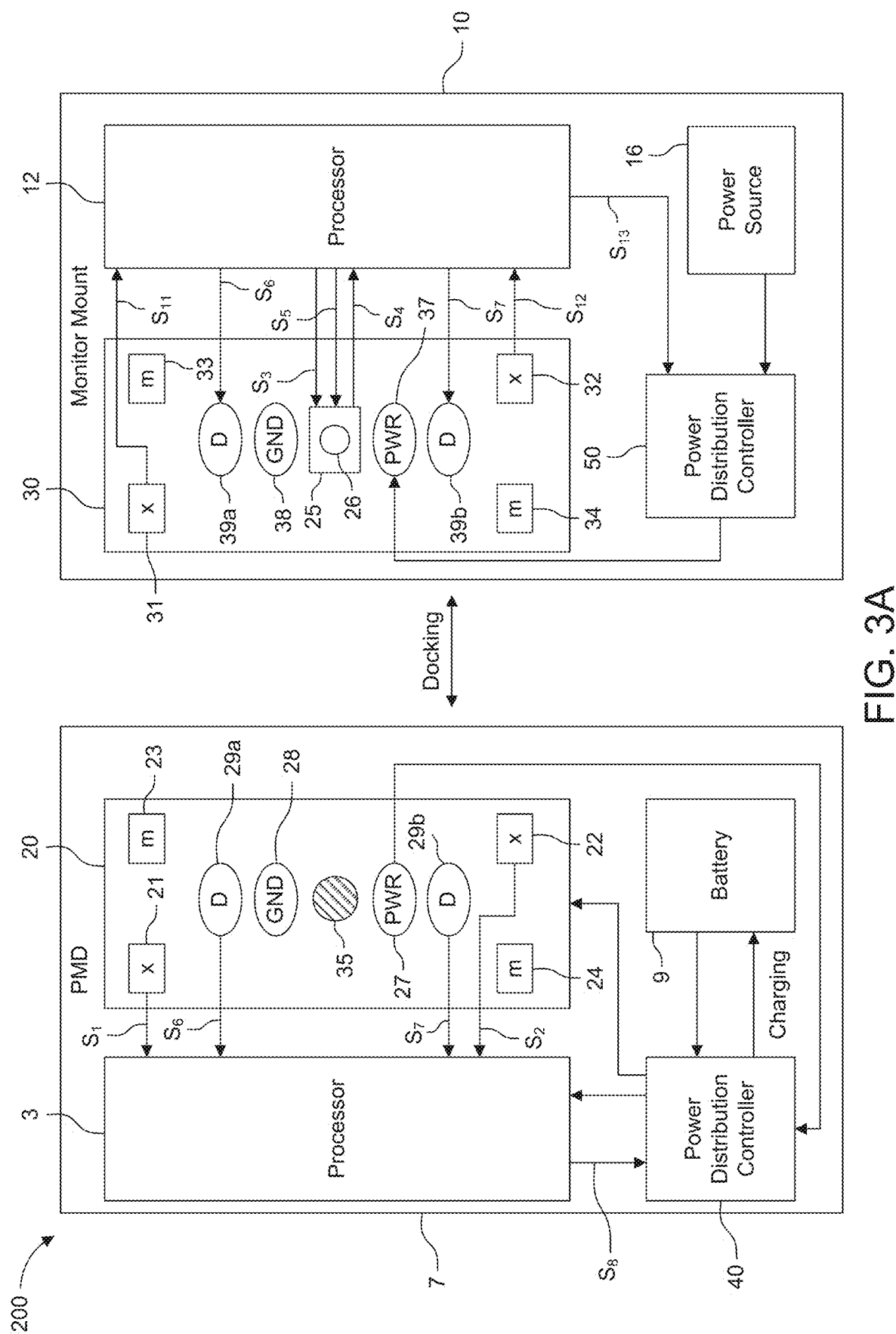
FIG. 3A is a schematic block diagram of a docking system 200 according to one or more embodiments.

FIG. 3A is a schematic block diagram of a docking system 200 according to one or more embodiments. The docking system 200 is similar to docking system 100 except the OLM 25 and the reflective structure 35 swap locations. Thus, the docking interface 20 of the patient monitor 7 includes the reflective structure 35 and the docking interface 30 of the monitor mount 10 includes the OLM 25 and bi-directional diode 26. Also, sensor elements 21 and 22 and magnets 33 and 34 are not used in this configuration and could be removed.

The processor 12 is configured to generate signals S3 and S5 and receive signals S4 in a similar manner described above. In particular, the processor 12 uses magnetic field sensor elements 31 and 32 for proximity detection during docking and undocking maneuvers in a similar manner processor 3 of docking system 100 uses magnetic field sensor elements 21 and 22. Thus, in response to at least one of the sensor signals S11 and S12 equaling or exceeding the proximity threshold value, processor 12 transmits an enable control signal S5 to the OLM 25 to enable the bi-directional diode 26. If the processor 12 then detects a predetermined number N of reflected transmission signals or a predetermined percentage, the processor transmits a disable control signal S5 to the OLM 25 to disable the bi-directional diode 26.

The processor 12 also monitors the sensor signals S11 and S12 for triggering docked signals S6 and S7 and the connection of power source 16 to the power contact 37. As described above, when at least one of the sensor signals S11 and S12 is equal to or greater than the proximity threshold value, processor 12 generates docked signals S6 and S7 and enables the connection of power source 16 to the power contact 37. When the sensor signals S11 and S12 are less than the proximity threshold value, processor 12 disables the docked signals S6 and S7 and disconnects the power source 16 from the power contact 37.

The processor 3 also monitors for the docked signals S6 and S7 and connects the power source 9 to the power contact 27 via control signal S8 when at least one is detected. The processor 3 disconnects the power source 9 from the power contact 27 via control signal S8 when both are not detected.

The undocking maneuver is also performed in a similar manner to that described above. When the magnitudes of sensor signals S11 and S12 become less than the proximity threshold value, the processor 12 determines that undocking is complete and transmits an enable control signal S5 to the OLM 25 to enable the bi-directional diode 26. The bi-directional diode 26 then starts to transmit light pulses in search for another OLM to communicate with. During this transmission of light pulses, the processor 12 monitors for optical traffic, including optical transmission signals from another OLM or reflected transmission signals. If the processor 12 detects optical traffic from another OLM within a predetermined time period, an optical link is established between the two OLMs and optical communication continues. If reflected transmission signals are detected, the processor 12 may start the docking process again. On the other hand, if the processor 12 does not detect optical traffic within the predetermined time period, the processor 12 transmits a disable control signal S5 to the OLM 25 to disable the bi-directional diode 26 as optical transmissions are not needed.

Furthermore, in response to detecting the undocking event, processor 3 disconnects the power source 9 from the power contact 27. This occurs when processor 3 no longer detects the docked signals S6 and S7. In addition, processor 12 disconnects power source 16 from power contact 37. This occurs when processor 12 detects that the magnitudes of sensor signals S11 and S12 have become less than the proximity threshold value. The processor 12 may also cease generation the docked signals S6 and S7 in response to the magnitudes of both sensor signals S11 and S12 becoming less than the proximity threshold value.

Figure 3B:
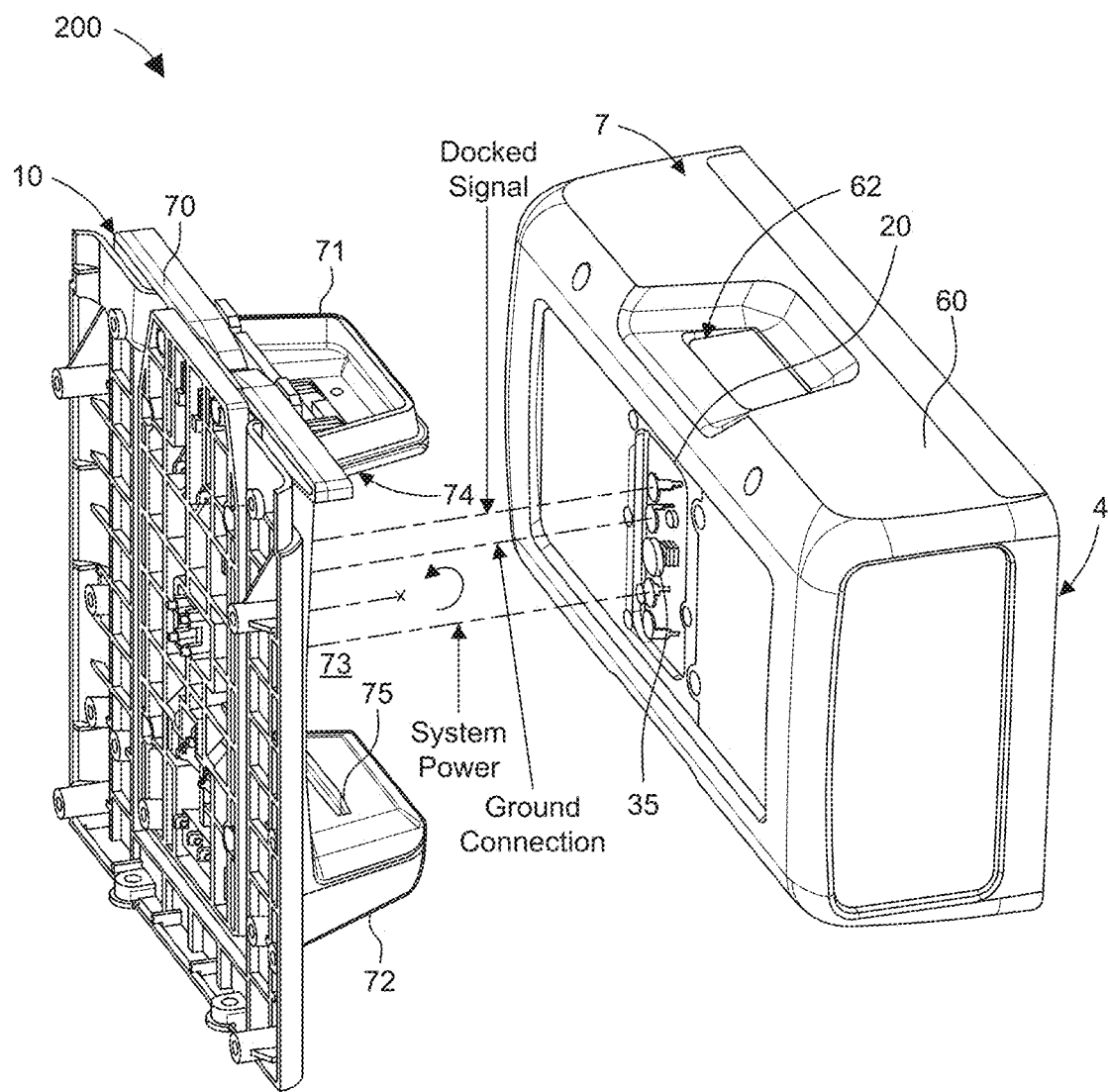
FIGS. 3B and 3C are perspective views of docking system 200 according to one or more embodiments.
Figure 3C:
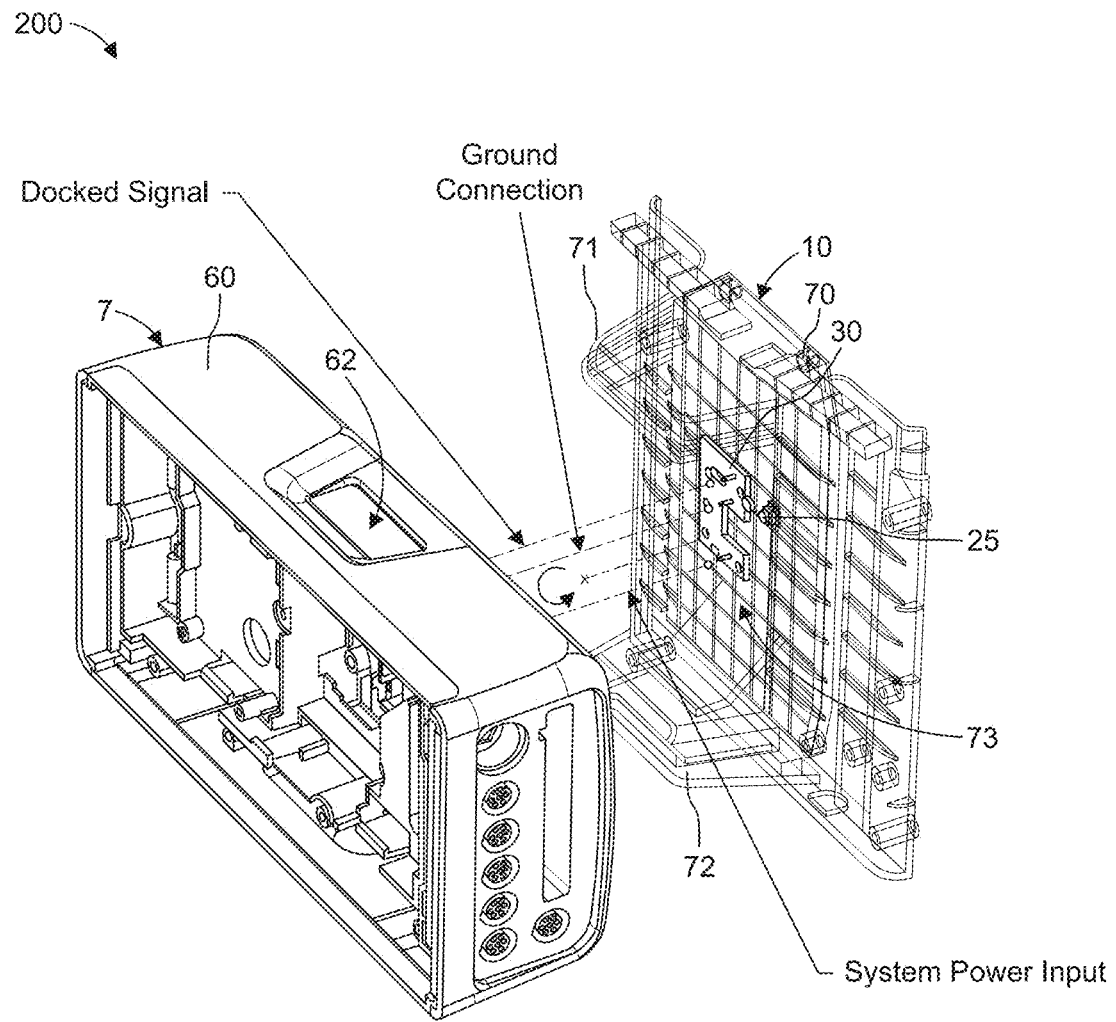

FIGS. 3B and 3C are perspective views of docking system 200 according to one or more embodiments. The housing 60 of the patient monitor 7 and the housing 70 of the monitor mount 10 are similar to those described above in reference to FIGS. 2B and 2C.

Figure 4A:
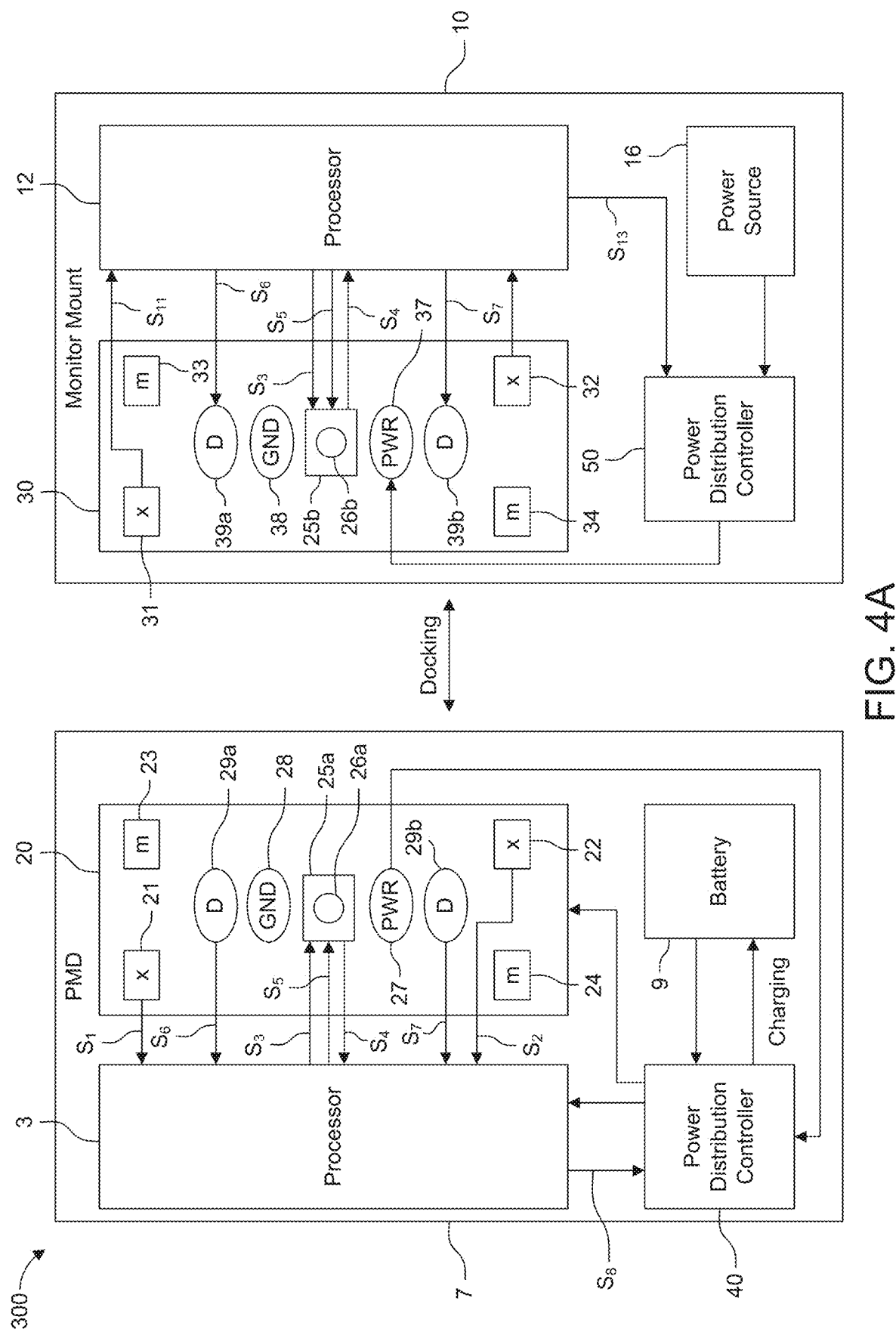
FIG. 4A is a schematic block diagram of a docking system 300 according to one or more embodiments.

FIG. 4A is a schematic block diagram of a docking system 300 according to one or more embodiments. The docking system 300 is similar to docking systems 100 and 200 in the sense that both docking interfaces 20 and 30 include an OLM and bi-directional diode. Thus, the OLM and bi-directional diode of docking interface 20 are referred to as OLM 25a and bi-directional diode 26a, while the OLM and bi-directional diode of docking interface 30 are referred to as OLM 25b and bi-directional diode 26b.

Proximity detection by processor 3 is performed using sensor signals S1 and S2 is used to enable and disable the bi-directional diode 26a. Similarly, proximity detection by processor 12 is performed using sensor signals S11 and S12 is used to enable and disable the bidirectional diode 26b. When proximity is detected by processor 3, processor 3 enables bi-directional diode 26a and bi-directional diode 26a starts transmitting light pulses in search of an optical link with another OLM. Likewise, when proximity is detected by processor 12, processor 12 enables bi-directional diode 26b and bi-directional diode 26b starts transmitting light pulses in search of an optical link with another OLM. In a docking maneuver, the two OLMs 25a and 25b will receive each other transmission signals (no reflected transmission signals) and the processors 3 and 12 will establish a communication link with each other.

In response to the patient monitor being undocked, if the processor 3 does not detect optical traffic received by the OLM 25a within a predetermined time period based on a counter value, the processor 3 may transmit a disable control signal S5 to the OLM 25a to disable the bi-directional diode 26a. Likewise, in response to the patient monitor being undocked, if the processor 12 does not detect optical traffic received by the OLM 25b within a predetermined time period based on a counter value, the processor 12 may transmit a disable control signal S5 to the OLM 25b to disable the bi-directional diode 26b.

The other aspects of docking system 300, including those related to energizing contacts and power distribution, are similar to those described above.

Figure 4B:
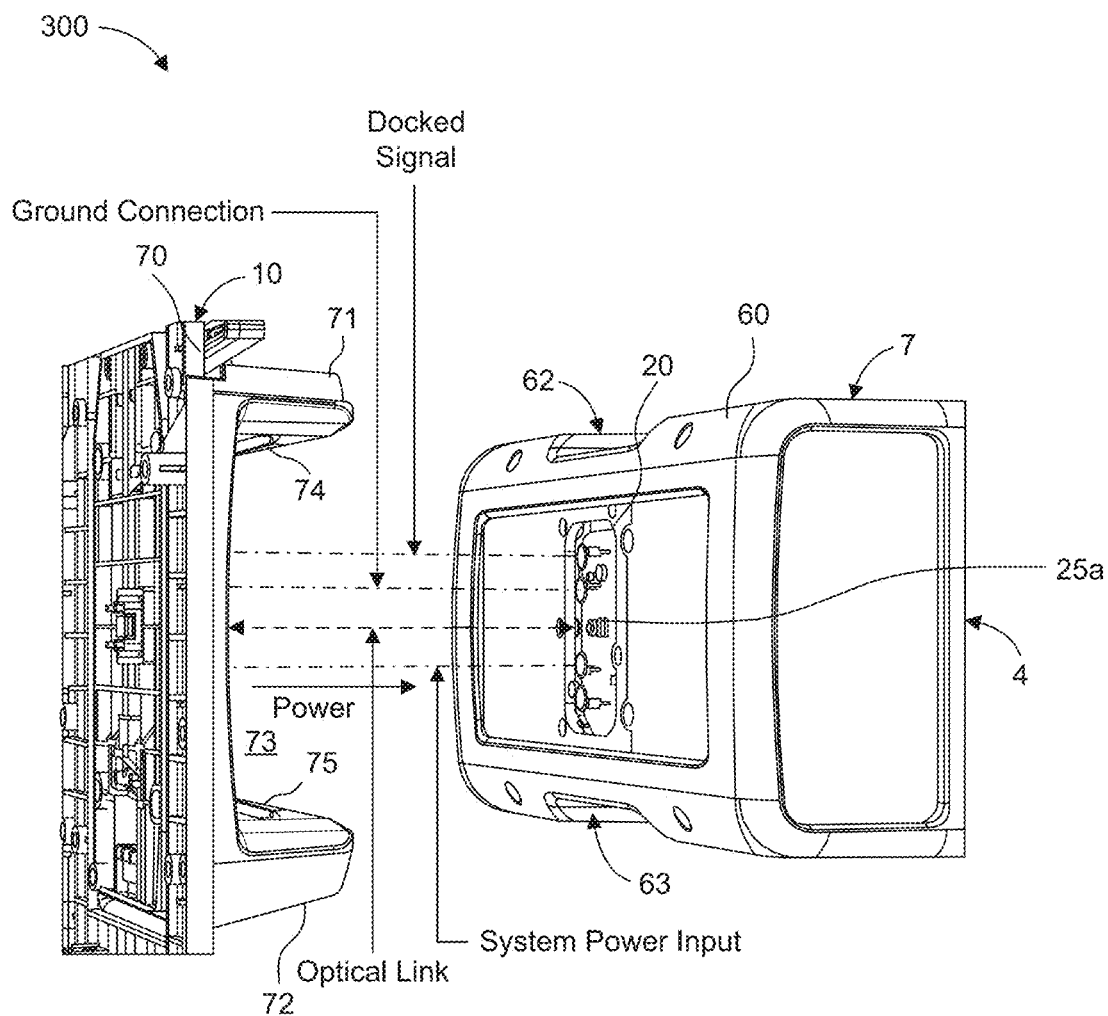
FIGS. 4B and 4C are perspective views of docking system 300 according to one or more embodiments.
Figure 4C:
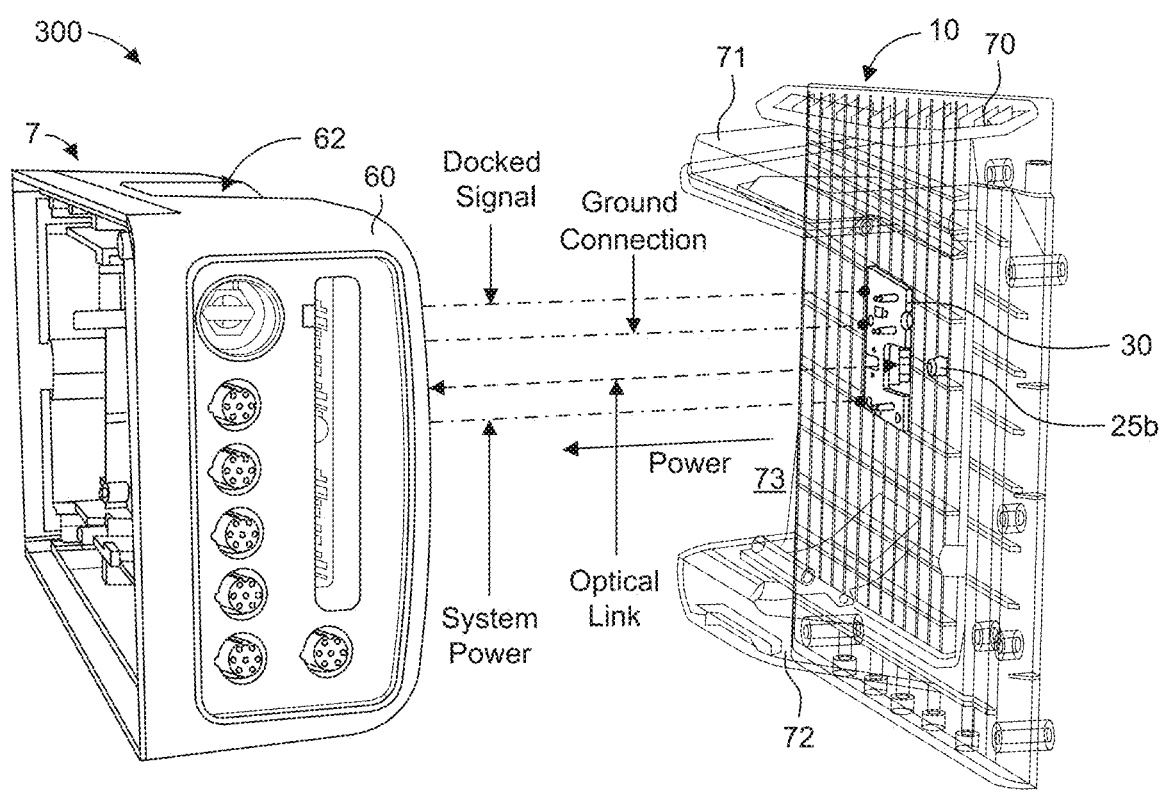

FIGS. 4B and 4C are perspective views of docking system 300 according to one or more embodiments. The housing 60 of the patient monitor 7 and the housing 70 of the monitor mount 10 are similar to those described above in reference to FIGS. 2B and 2C. However, here, OLMs 25a and 25b establish a bi-directional optical link with each other.

Figure 5A:
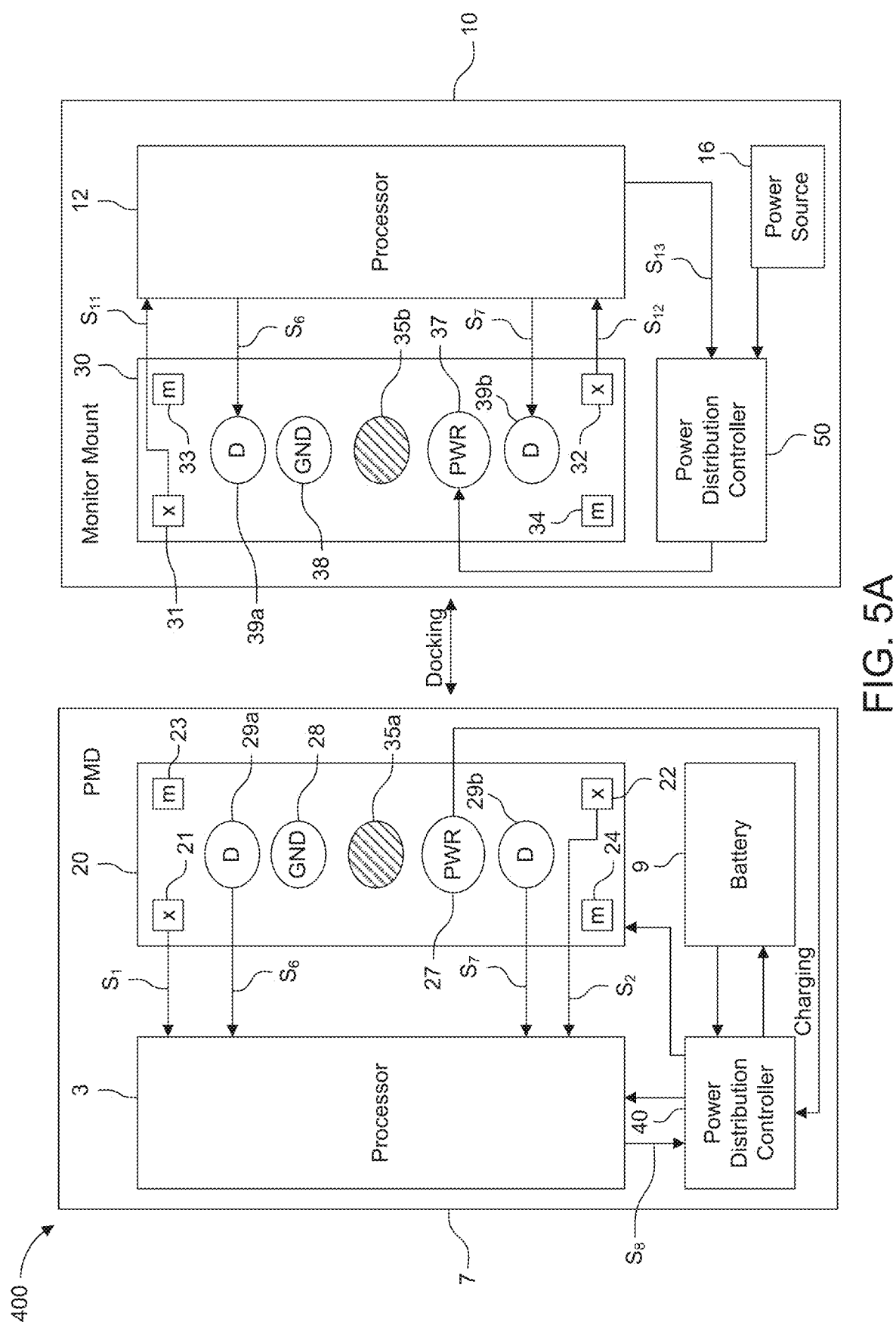
FIG. 5A is a schematic block diagram of a docking system 400 according to one or more embodiments.

FIG. 5A is a schematic block diagram of a docking system 400 according to one or more embodiments. The docking system 400 is similar to docking systems 100 and 200 in the sense that both docking interfaces 20 and 30 include a mirror structure 35a and 35b, respectively. Optionally, sensor elements 21, 22, 31, and 32 and magnets 23, 24, 33, and 34 are not used in this configuration and could be removed. Here, no optical communication exists and the patient monitor 7 uses the monitor mount 10 as a charging station.

Accordingly, proximity detection is implemented by processor 12 in the same way described in conjunction with FIG. 2A for energizing contacts and distributing power. Meanwhile, processor 3 monitors for the docked signals S6 and S7 and connects the power source 9 to the power contact 27 via control signal S8 when at least one is detected. The processor 3 disconnects the power source 9 from the power contact 27 via control signal S8 when both are not detected.

Thus, energizing contacts and distributing power at both the patient monitor 7 and the monitoring mount 10 are performed in a similar manner as described in the previous embodiments.

Figure 5B:
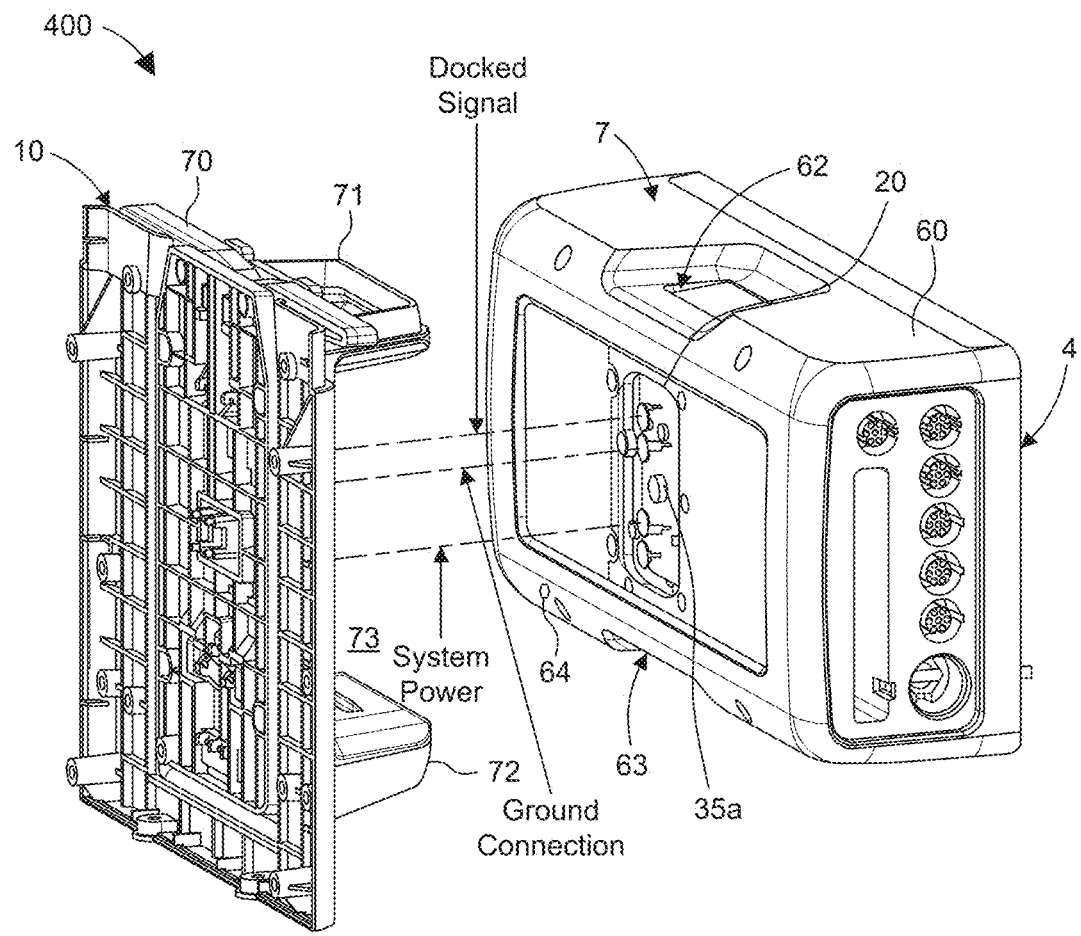
FIGS. 5B and 5C are perspective views of docking system 400 according to one or more embodiments.
Figure 5C:
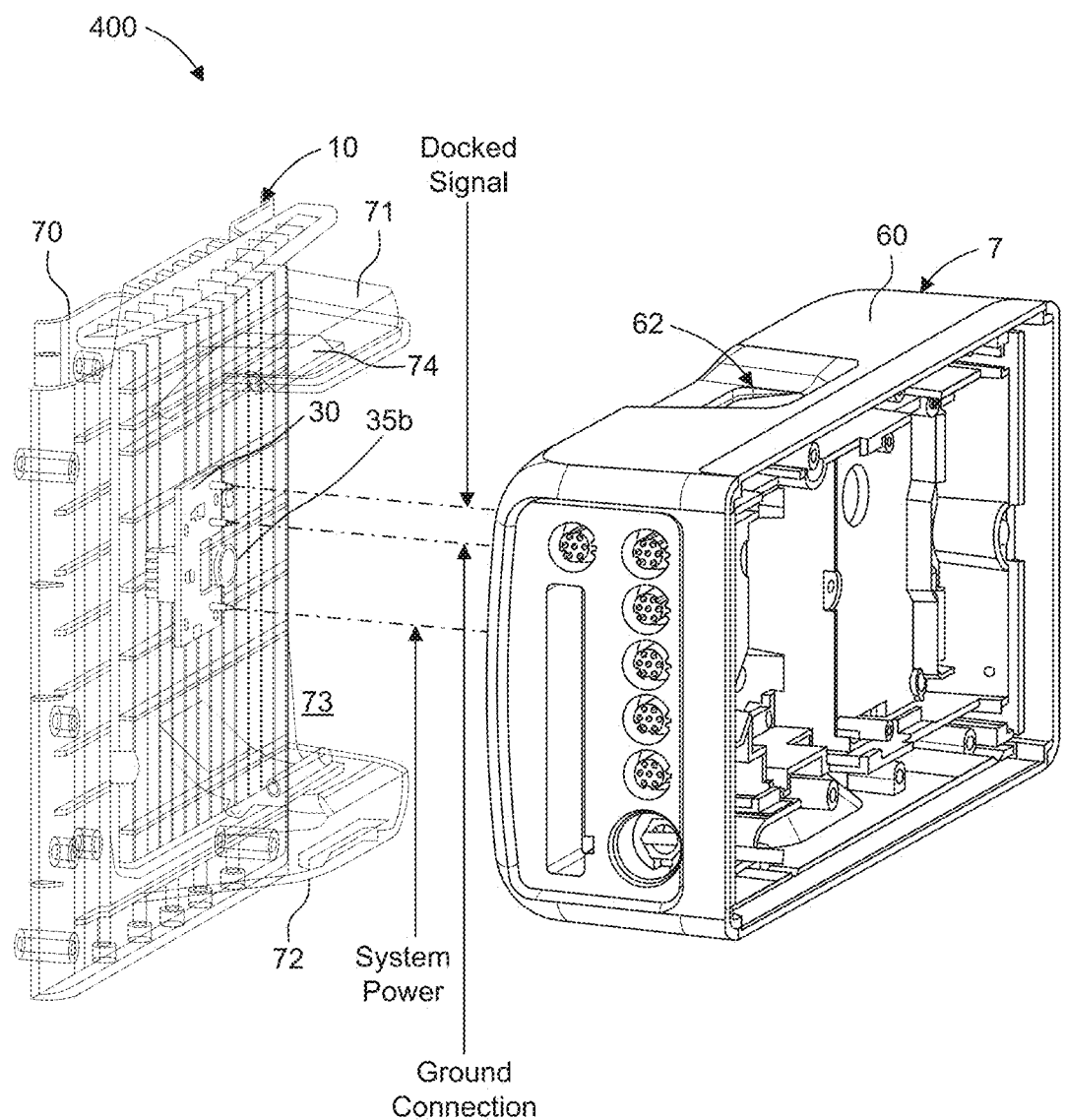

FIGS. 5B and 5C are perspective views of docking system 400 according to one or more embodiments. The housing 60 of the patient monitor 7 and the housing 70 of the monitor mount 10 are similar to those described above in reference to FIGS. 2B and 2C. However, here, the PMM device 7 and the monitor mount 10 both include reflective structures 35a and 35b.

Figure 6:
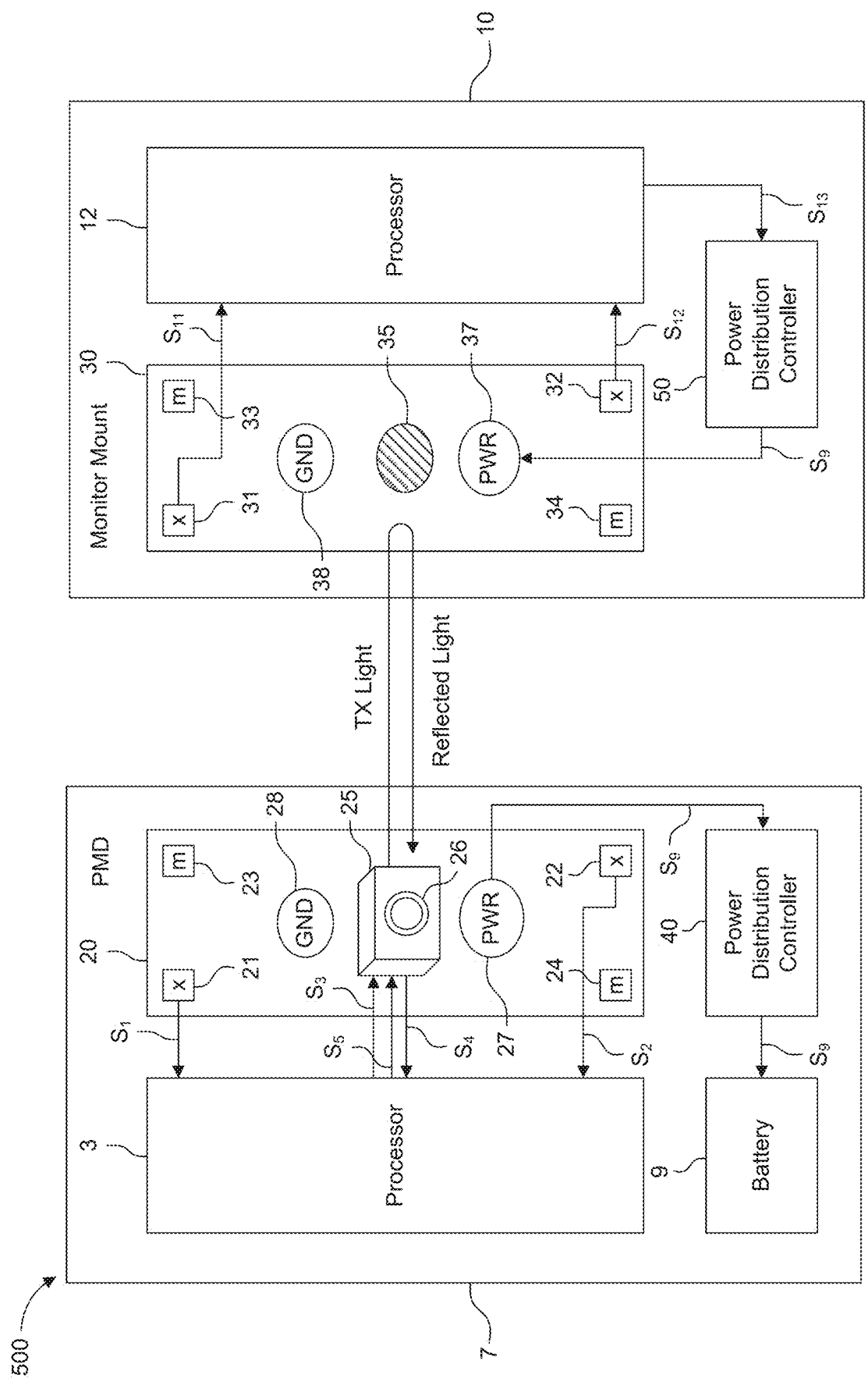
FIG. 6 is a schematic block diagram of a docking system 500 according to one or more embodiments.

FIG. 6 is a schematic block diagram of a docking system 500 according to one or more embodiments. The docking system 500 is similar to docking system 100 with the exception that docked signal contacts 29a, 29b, 39a, and 39b are not present. Instead, the power contacts 27 and 37 are used for detecting that docking has been completed or that undocking has been initiated. In particular, power contact 27 is used by the patient monitor 7 to both supply power from the monitor mount 10 to the power source 9 (e.g., for recharging the battery) and for detecting that docking has been completed or that undocking has been initiated. Thus, power contacts 27 and 37 serve as docked signal contacts.

Like before, processor 3 compares the values of sensor signals S1 and S2 to a proximity threshold value to monitor for docking and undocking events. During a docking maneuver, processor 3 detects a docking event when both sensor signals S1 and S2 are equal to or greater than the proximity threshold value. In response to detecting the docking event, the processor 3 transmits an enable control signal S5 to enable the bi-directional diode 26. While one of the sensor signals S1 and S2 may be sufficient for triggering proximity detection, requiring both to be simultaneously equal to or greater than the proximity threshold value provides a higher confidence that interface 20 is in a docking maneuver with interface 30.

Once enabled, the OLM 25 enables the bi-directional diode 26 to transmit sequential light pulses in search for another OLM to establish a communication link therewith. However, if the processor 3 detects a predetermined number N of reflected transmission signals due to reflections by the reflective structure 35, the processor 3 determines that optical communications are not needed and transmits a disable control signal S5 to the OLM 25 to disable the bi-directional diode 26. Here, N is an integer greater than one. Alternatively, the processor 3 may monitor for a predetermined percentage of reflections where the predetermined percentage may be 80% or greater. In other words, the threshold may be met when 80% of the transmitted light pulses are detected as reflected pulses. Thus, multiple reflected transmission signals should be received before disabling the bi-directional diode 26.

In addition, when docking between interfaces 20 and 30 is complete, power contact 27 is in contact with power contact 37 and receives a power signal S9 therefrom. The power distribution controller 40 is configured to monitor the value of the power signal S9 can compare it to a power signal threshold. The power signal threshold may be a voltage value or a current value. When the value of the power signal S9 meets or exceeds the power signal threshold, the power distribution controller 40 is configured to route the power signal S9 to the power source 9 (e.g., via closing a switch) to recharge the battery.

Similarly, processor 12 also performs its own proximity detection. In response to the magnitude of both sensor signals S11 and S12 becoming equal to or greater than the proximity threshold value, processor 12 generates power distribution enable signal S13 that instructs the power distribution controller 50 to provide power via power signal 9 to the power contact 37. The power signal 9 is then received by power contact 27.

In the event that the magnitudes of one or both sensor signals S11 and S12 become less than the proximity threshold value indicating, for example, that docking was aborted or that an undocking maneuver is being performed, the processor 12 is configured to send a power distribution disable signal S13 that instructs the power distribution controller 50 to stop routing the power signal 9 to the power contact 37.

In the event that the power distribution controller 40 detects that the power signal 9 is less than the power signal threshold, the power distribution controller 40 may assume that the patient monitor 7 has been separated from the monitor mount 10. In this case, the power distribution controller 40 may disconnect power contact 27 from the power source 9.

The remaining undocking processes are similar to those described above in conjunction with FIG. 2A.

Figure 7:
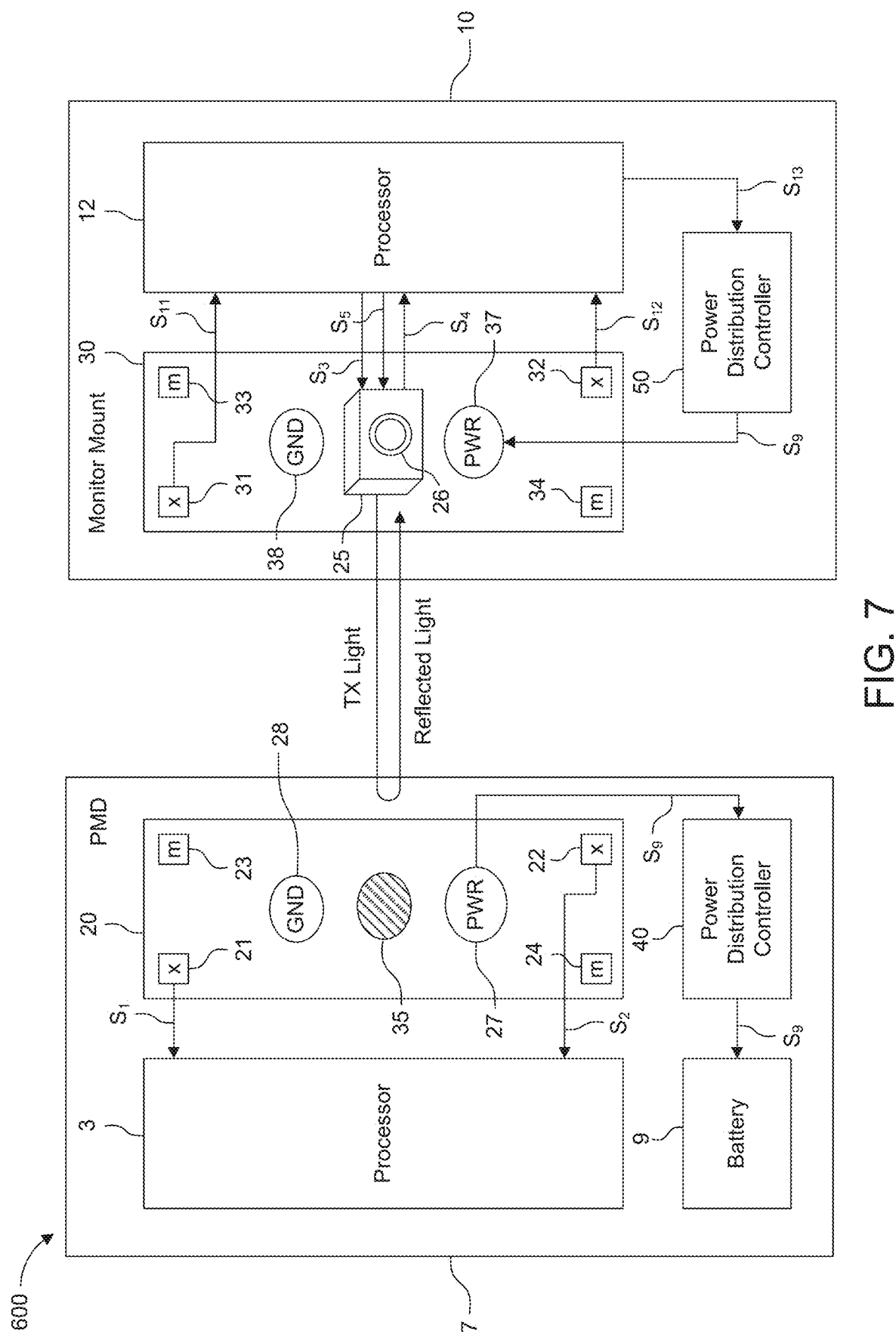
FIG. 7 is a schematic block diagram of a docking system 600 according to one or more embodiments.

FIG. 7 is a schematic block diagram of a docking system 600 according to one or more embodiments. The docking system 600 is similar to docking system 200 with the exception that docked signal contacts 29a, 29b, 39a, and 39b are not present. Instead, the power contacts 27 and 37 are used for detecting that docking has been completed or that undocking has been initiated. In particular, power contact 27 is used by the patient monitor 7 to both supply power from the monitor mount 10 to the power source 9 (e.g., for recharging the battery) and for detecting that docking has been completed or that undocking has been initiated. Thus, power contacts 27 and 37 serve as docked signal contacts. As a result, the differences between docking systems 200 and 600 are similar to the differences between docking systems 100 and 500.

In response to both the sensor signals S11 and S12 equaling or exceeding the proximity threshold value, processor 12 transmits an enable control signal S5 to the OLM 25 to enable the bi-directional diode 26. If the processor 12 then detects a predetermined number N of reflected transmission signals or a predetermined percentage, the processor 12 transmits a disable control signal S5 to the OLM 25 to disable the bi-directional diode 26.

The processor 12 also monitors the sensor signals S11 and S12 for triggering power signal 9 to be routed to the power contact 37. As described above, when both of the sensor signals S11 and S12 is equal to or greater than the proximity threshold value, processor 12 instructs the power distribution controller 50 via signal 13 to route the power signal 9 to the power contact 37. When the sensor signals S11 and S12 are less than the proximity threshold value, processor 12 instructs the power distribution controller 50 via signal 13 to cease routing the power signal 9 to the power contact 37.

The power distribution controller 40 also monitors for the power signal S9 and connects the power source 9 to the power contact 27 when the power signal S9 meets or exceeds a power signal threshold. The power distribution controller 40 disconnects the power source 9 from the power contact 27 when the power signal S9 does not meet or exceed the power signal threshold.

The remaining docking and undocking processes are similar to those described above in conjunction with FIG. 3A.

Figure 8:
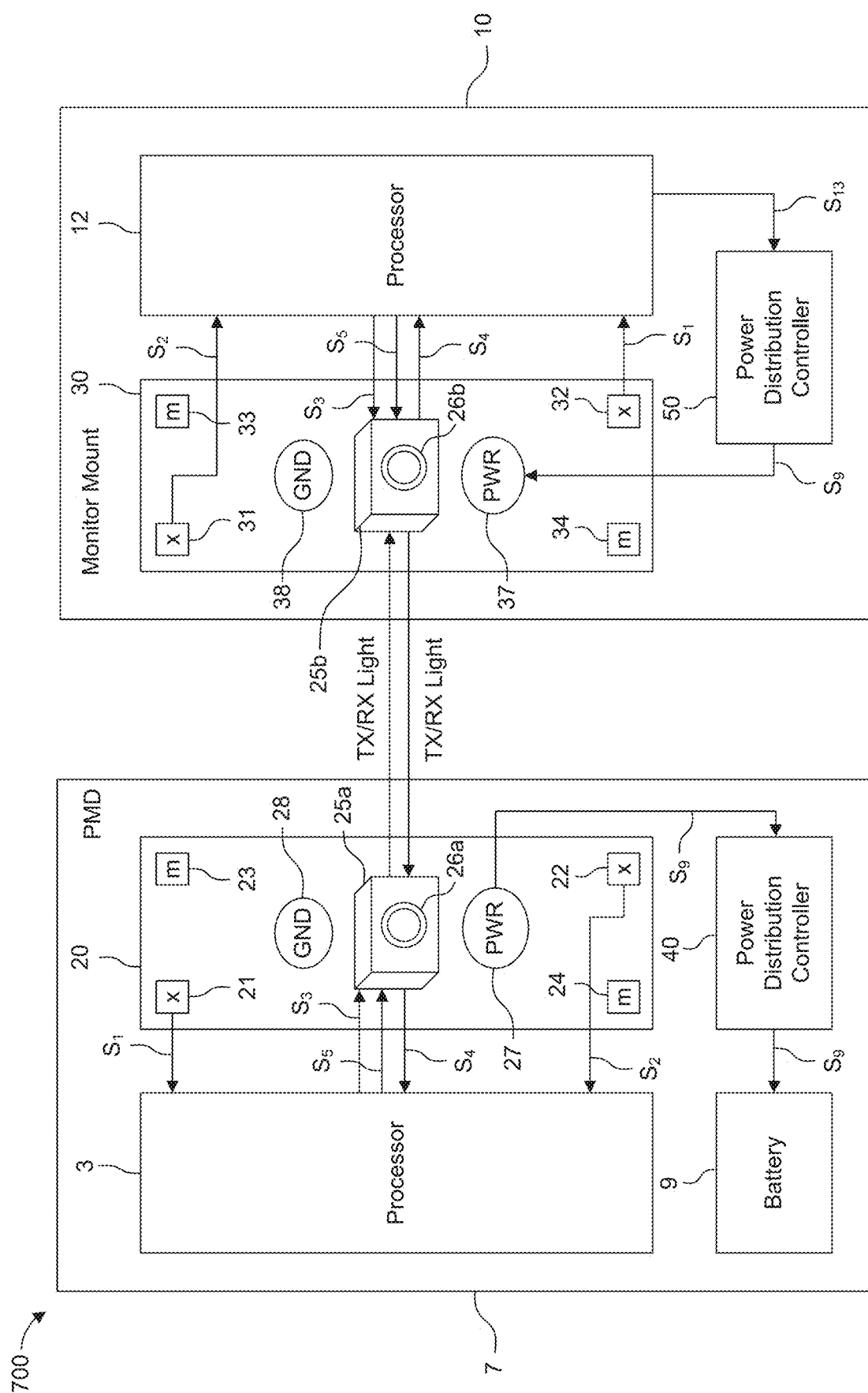
FIG. 8 is a schematic block diagram of a docking system 700 according to one or more embodiments.

FIG. 8 is a schematic block diagram of a docking system 700 according to one or more embodiments. The docking system 700 is similar to docking system 300 with the exception that docked signal contacts 29a, 29b, 39a, and 39b are not present. Instead, the power contacts 27 and 37 are used for detecting that docking has been completed or that undocking has been initiated. In particular, power contact 27 is used by the patient monitor 7 to both supply power from the monitor mount 10 to the power source 9 (e.g., for recharging the battery) and for detecting that docking has been completed or that undocking has been initiated. Thus, power contacts 27 and 37 serve as docked signal contacts. As a result, the differences between docking systems 300 and 700 are similar to the differences between docking systems 100 and 500.

Proximity detection by processor 3 is performed using sensor signals S1 and S2 is used to enable and disable the bi-directional diode 26a. Similarly, proximity detection by processor 12 is performed using sensor signals S11 and S12 is used to enable and disable the bidirectional diode 26b. When proximity is detected by processor 3, processor 3 enables bi-directional diode 26a and bi-directional diode 26a starts transmitting light pulses in search of an optical link with another OLM. Likewise, when proximity is detected by processor 12, processor 12 enables bi-directional diode 26b and bi-directional diode 26b starts transmitting light pulses in search of an optical link with another OLM. In a docking maneuver, the two OLMs 25a and 25b will receive each other transmission signals (no reflected transmission signals) and the processors 3 and 12 will establish a communication link with each other.

In response to the patient monitor being undocked, if the processor 3 does not detect optical traffic received by the OLM 25a within a predetermined time period based on a counter value, the processor 3 may transmit a disable control signal S5 to the OLM 25a to disable the bi-directional diode 26a. Likewise, in response to the patient monitor being undocked, if the processor 12 does not detect optical traffic received by the OLM 25b within a predetermined time period based on a counter value, the processor 12 may transmit a disable control signal S5 to the OLM 25b to disable the bi-directional diode 26b.

In addition, when docking between interfaces 20 and 30 is complete, power contact 27 is in contact with power contact 37 and receives a power signal S9 therefrom. The power distribution controller 40 is configured to monitor the value of the power signal S9 can compare it to a power signal threshold. The power signal threshold may be a voltage value or a current value. When the value of the power signal S9 meets or exceeds the power signal threshold, the power distribution controller 40 is configured to route the power signal S9 to the power source 9 (e.g., via closing a switch) to recharge the battery.

Similarly, processor 12 also performs its own proximity detection. In response to the magnitude of both sensor signals S11 and S12 becoming equal to or greater than the proximity threshold value, processor 12 generates power distribution enable signal S13 that instructs the power distribution controller 50 to provide power via power signal 9 to the power contact 37. The power signal 9 is then received by power contact 27.

In the event that the magnitudes of one or both sensor signals S11 and S12 become less than the proximity threshold value indicating, for example, that docking was aborted or that an undocking maneuver is being performed, the processor 12 is configured to send a power distribution disable signal S13 that instructs the power distribution controller 50 to stop routing the power signal 9 to the power contact 37.

In the event that the power distribution controller 40 detects that the power signal 9 is less than the power signal threshold, the power distribution controller 40 may assume that the patient monitor 7 has been separated from the monitor mount 10. In this case, the power distribution controller 40 may disconnect power contact 27 from the power source 9.

The remaining docking and undocking processes are similar to those described above in conjunction with FIG. 4A.

Figure 9:
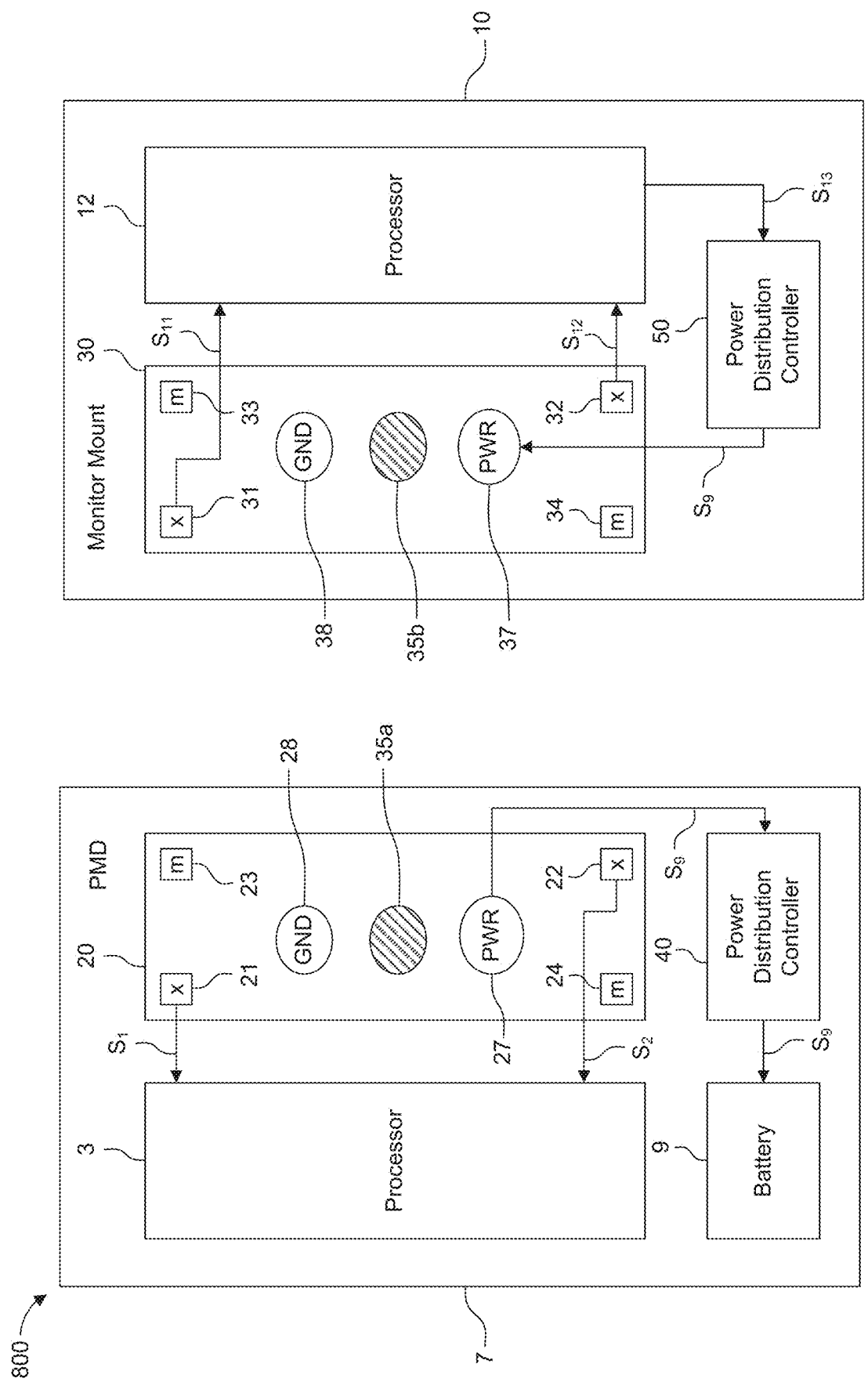
FIG. 9 is a schematic block diagram of a docking system 800 according to one or more embodiments.

FIG. 9 is a schematic block diagram of a docking system 800 according to one or more embodiments. The docking system 800 is similar to docking system 400 with the exception that docked signal contacts 29a, 29b, 39a, and 39b are not present. Instead, the power contacts 27 and 37 are used for detecting that docking has been completed or that undocking has been initiated. In particular, power contact 27 is used by the patient monitor 7 to both supply power from the monitor mount 10 to the power source 9 (e.g., for recharging the battery) and for detecting that docking has been completed or that undocking has been initiated. Thus, power contacts 27 and 37 serve as docked signal contacts. As a result, the differences between docking systems 400 and 800 are similar to the differences between docking systems 100 and 500.

When docking between interfaces 20 and 30 is complete, power contact 27 is in contact with power contact 37 and receives a power signal S9 therefrom. The power distribution controller 40 is configured to monitor the value of the power signal S9 can compare it to a power signal threshold. The power signal threshold may be a voltage value or a current value. When the value of the power signal S9 meets or exceeds the power signal threshold, the power distribution controller 40 is configured to route the power signal S9 to the power source 9 (e.g., via closing a switch) to recharge the battery.

Similarly, processor 12 also performs its own proximity detection. In response to the magnitude of both sensor signals S11 and S12 becoming equal to or greater than the proximity threshold value, processor 12 generates power distribution enable signal S13 that instructs the power distribution controller 50 to provide power via power signal 9 to the power contact 37. The power signal 9 is then received by power contact 27.

In the event that the magnitudes of one or both sensor signals S11 and S12 become less than the proximity threshold value indicating, for example, that docking was aborted or that an undocking maneuver is being performed, the processor 12 is configured to send a power distribution disable signal S13 that instructs the power distribution controller 50 to stop routing the power signal 9 to the power contact 37.

In the event that the power distribution controller 40 detects that the power signal 9 is less than the power signal threshold, the power distribution controller 40 may assume that the patient monitor 7 has been separated from the monitor mount 10. In this case, the power distribution controller 40 may disconnect power contact 27 from the power source 9.

The remaining docking and undocking processes are similar to those described above in conjunction with FIG. 5A.

Figure 10A:
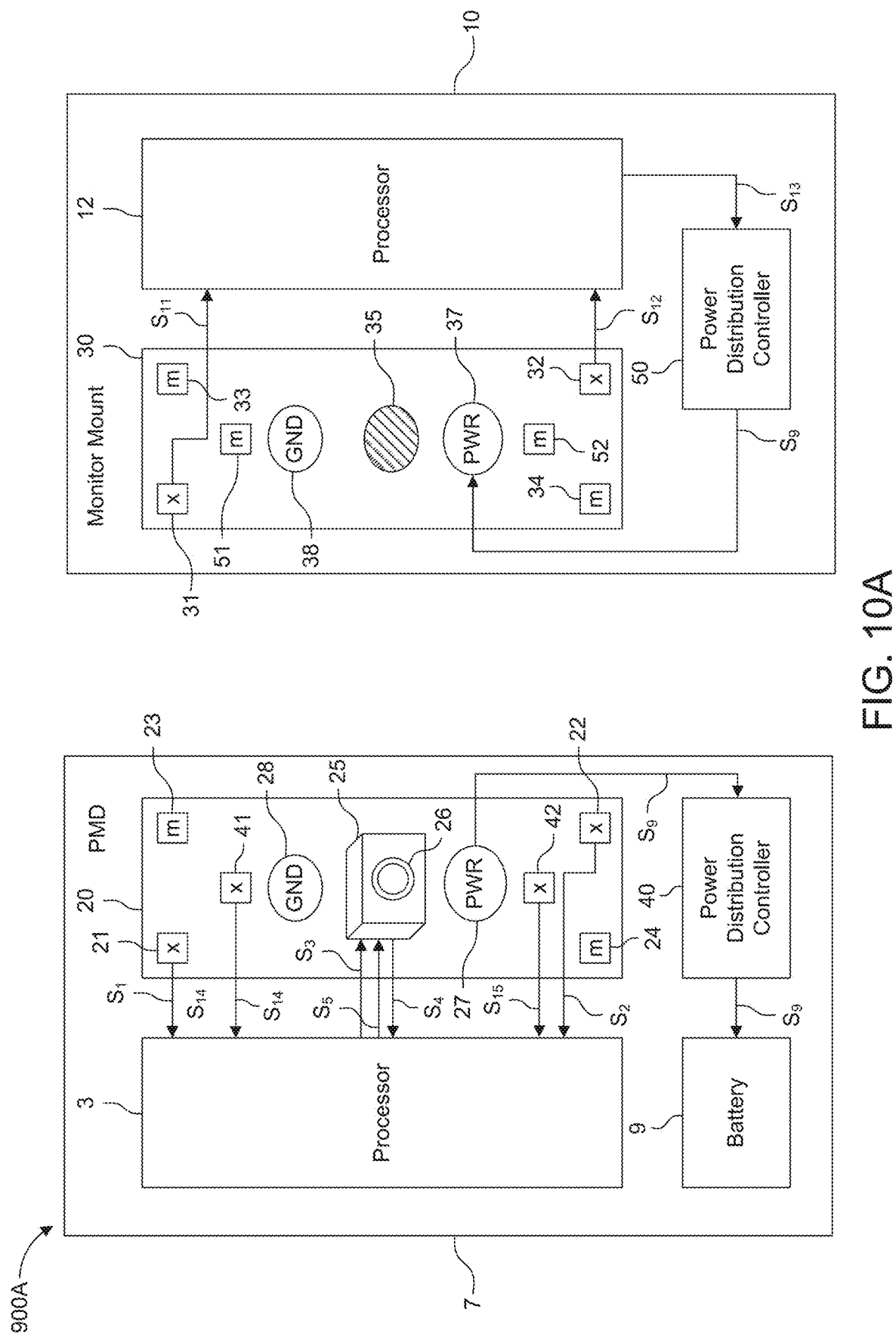
FIGS. 10A and 10B are schematic block diagrams of docking systems 900A and 900B according to one or more embodiments.
Figure 10B:
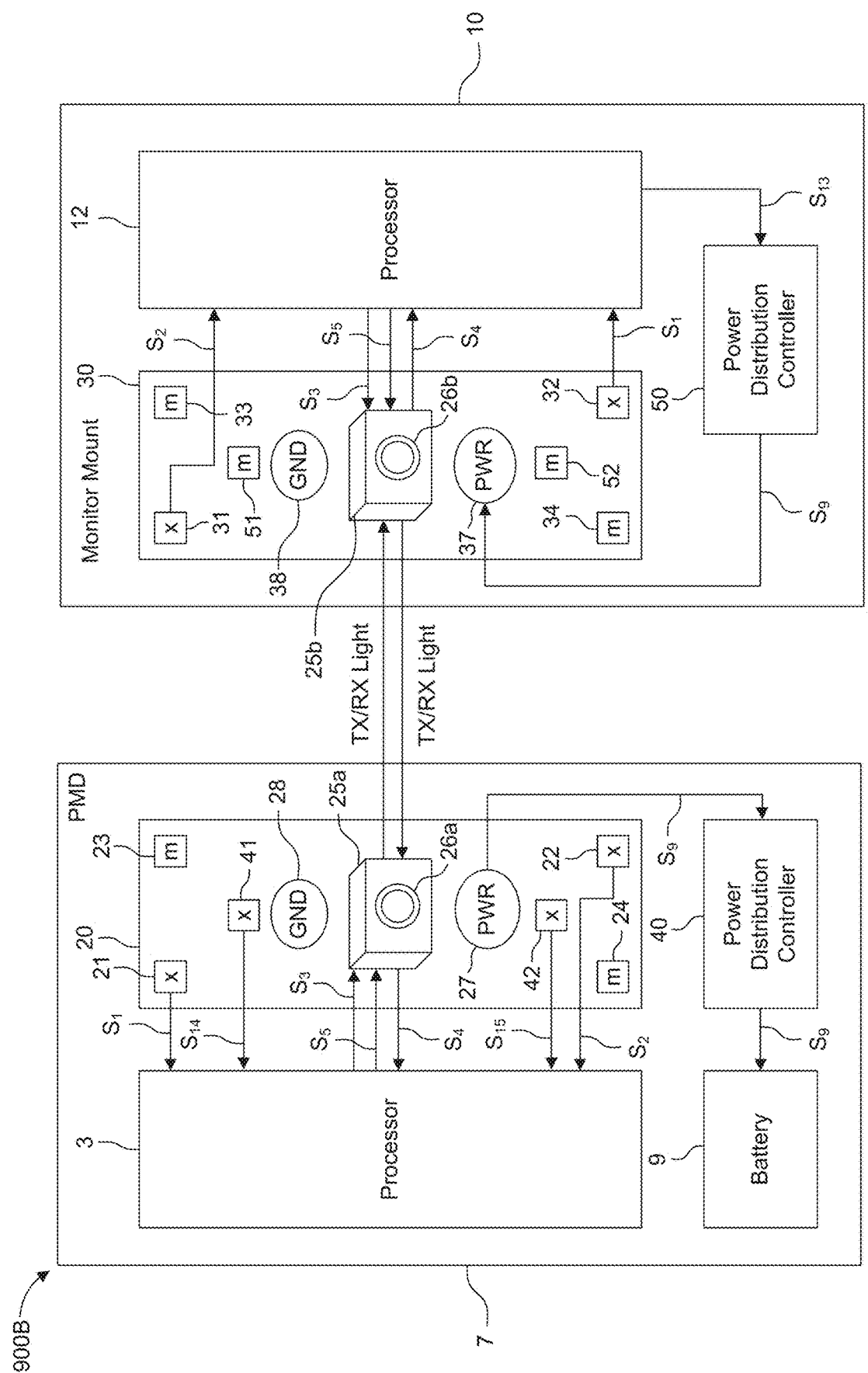

FIGS. 10A and 10B are schematic block diagrams of docking systems 900A and 900B according to one or more embodiments. In docking systems 900A and 900B, the patient monitor 7 is configured to determine the type of monitor mount 10 to which it is being docked based on the presence or absence of additional magnetic fields and enable or disable its bi-directional diode 26, 26a based on the determined type of monitor mount. The monitor mount 10 may be of a first type that includes a reflective structure 35 and thus no OLM for optical communication or may be of a second type that includes an OLM 25b for optical communication. If the patient monitor 7 detects that the monitor mount 10 is the first type, it may disable the bi-directional diode 26, 26a during a docking maneuver. In contrast, if the patient monitor 7 detects that the monitor mount 10 is the second type, it may enable the bi-directional diode 26, 26a during a docking maneuver.

The interface 20 of the patient monitor 7 includes additional sensor elements 41 and 42 that are arranged to allow for detection during non-inverted and inverted docking maneuvers. The additional sensor elements 41 and 42 are spatially arranged within the docking interface 20 to detect the presence of additional magnetic fields that may be generated by additional magnets 51 and 52, if present on the monitor mount 10, or detect the absence of additional magnets 51 and 52, if absent from the monitor mount 10.

Magnetic field sensor elements 41 and 42 that generate sensor signals S14 and S15 corresponding to a measured magnetic field and provide the sensor signals to the processor 3 for processing and evaluation. The processor 3 is configured to compare the value (e.g., magnitude) of the sensor signals to a proximity threshold value and provide further action based on the comparison result. For example, if the value of the sensor signals are equal to or greater than the proximity threshold value during a docking maneuver, the processor 3 determines that the monitor mount 10 is the first type or the second type depending on whether the docking interface 30 has an additional magnet configuration as shown in FIG. 10A or as shown in FIG. 10B. If the value of the sensor signals are less than the proximity threshold value during a docking maneuver, the processor 3 determines that the monitor mount 10 is the first type or the second type depending on whether the docking interface 30 has an additional magnet configuration as shown in FIG. 10A or as shown in FIG. 10B.

The processor 3 may trigger an evaluation of the monitor mount type based on its evaluation of signals S1 and S2. For example, if the processor 3 detects a docking event according to signals S1 and S2 meeting or exceeding the proximity threshold value, as described above, the processor 3 may trigger an evaluation of signals S14 and S15 to determine the monitor mount type in order to further determine whether to enable the bi-directional diode 26, 26a or whether to maintain the bi-directional diode 26, 26a in a disabled state. For example, if the processor 3 detects a docking event according to signals S1 and S2 meeting or exceeding the proximity threshold value and further detects that evaluation of signals S14 and S15 also meet or exceed the proximity threshold value, the processor 3 can determine the monitor mount type accordingly. In contrast, if the processor 3 detects a docking event according to signals S1 and S2 meeting or exceeding the proximity threshold value and further detects that evaluation of signals S14 and S15 do not meet or exceed the proximity threshold value, the processor 3 can determine the monitor mount type accordingly.

If the processor 3 detects a docking event, and then further determines that the monitor mount 10 is the first type (i.e., with no OLM), the processor 3 maintains the bi-directional diode 26, 26a in a disabled state. If the processor 3 detects a docking event, and then further determines that the monitor mount 10 is the second type (i.e., with an OLM), the processor 3 switches the bi-directional diode 26, 26a from a disabled state to an enabled state and the bi-directional diode 26, 26a starts transmitting optical signals in attempt to establish a communication link with the monitor mount 10.

FIG. 10A illustrates the case in which the monitor mount 10 is the first type that includes reflective structure 35 and thus no OLM. The monitor mount 10 being the first type also includes additional magnets 51 and 52 to indicate that it is the first type. Whereas, the second type does not include the additional magnets 51 and 52. If present, the additional magnets 51 and 52 should be substantially in spatial alignment with magnetic field sensor elements 41 and 42. Thus, to indicate that it is the first type of monitor mount, the monitor mount 10 includes additional magnets 51 and 52. In this case, a monitor mount of the second type would have a magnet arrangement as shown in FIGS. 4A and 8 (i.e., a magnet arrangement without additional magnets 51 and 52).

The processor 3 continuously monitors sensor signals S1 and S2 to detect a docking event in a similar manner described above. When the processor 3 detects a docking event, it triggers an evaluation of sensor signals S14 and S15 to determine the monitor mount type. If the sensor signals S14 and S15 also meet or exceed the proximity threshold value, the processor 3 determines that the monitor mount 10 is the first type and maintains the bi-directional diode 26, 26a in a disabled state during docking. If the sensor signals S14 and S15 are less than the proximity threshold value, the processor 3 determines that the monitor mount 10 is the second type and enables the bi-directional diode 26, 26a. Thus, the bi-directional diode 26 can be activated only when needed.

FIG. 10B illustrates the case in which the monitor mount 10 is the second type that includes OLM 25b and the second type includes additional magnets 51 and 52 to indicate that the monitor mount is the second type. Whereas, the first type does not include the additional magnets 51 and 52. If present, the additional magnets 51 and 52 should be substantially in spatial alignment with magnetic field sensor elements 41 and 42. Thus, to indicate that it is the second type of monitor mount, the monitor mount 10 includes additional magnets 51 and 52. In this case, a monitor mount of the first type would have a magnet arrangement as shown in FIGS. 2A and 6 (i.e., a magnet arrangement without additional magnets 51 and 52).

The processor 3 continuously monitors sensor signals S1 and S2 to detect a docking event in a similar manner described above. When the processor 3 detects a docking event, it triggers an evaluation of sensor signals S14 and S15 to determine the monitor mount type. If the sensor signals S14 and S15 also meet or exceed the proximity threshold value, the processor 3 determines that the monitor mount 10 is the second type and enables the bi-directional diode 26, 26a. If the sensor signals S14 and S15 are less than the proximity threshold value, the processor 3 determines that the monitor mount 10 is the first type and maintains the bi-directional diode 26, 26a in a disabled state during docking. Thus, the bi-directional diode 26 can be activated only when needed.

Additional embodiments are set forth below:

1. A docking interface configured to dock with another device, comprising:
   an optical link module comprising a transceiver configured to transmit and receive optical signals;
   a magnetic field sensor element configured to generate an electrical signal in response to a magnetic field impinging thereon; and
   at least one processor configured to receive the electrical signal, compare a magnitude of the electrical signal to a proximity threshold value to generate a comparison result, and detect a docking event and an undocking event based on the comparison result,
   wherein the at least one processor detects the docking event in response to detecting a first condition satisfied when the magnitude of the electrical signal increases such that it becomes equal to or greater than the proximity threshold value, and
   wherein the at least one processor detects the undocking event in response to detecting a second condition satisfied when the magnitude of the electrical signal decreases such that it becomes less than the proximity threshold value.

2. The docking interface of embodiment 1, wherein, in response to detecting the docking event, the at least one processor is configured to enable the transceiver to transmit optical signals.

3. The docking interface of embodiment 2, wherein:
   in response to enabling the transceiver during the docking event, the at least one processor is configured to monitor for reflected optical signals corresponding to the transmitted optical signals, the reflected optical signals being received at the transceiver, and
   in response to detecting a number of one or more reflected optical signals during the docking event, the at least one processor is configured to disable the transceiver.

4. The docking interface of embodiment 3, wherein the number of reflected optical signals is greater than one.

5. The docking interface of embodiment 2, wherein:
   in response to enabling the transceiver during the docking event, the at least one processor is configured to monitor for optical signals transmitted by the other device, the optical signals being received at the transceiver, and
   in response to detecting at least one optical signal transmitted by the other device during the docking event, the at least one processor is configured to establish an optical communication link with the other device.

6. The docking interface of embodiment 2, wherein:
   in response to enabling the transceiver during the docking event, the at least one processor is configured to monitor for received optical signals that are received at the transceiver and determine whether the received optical signals are reflected optical signals corresponding to the transmitted optical signals or optical signals transmitted by the other device.

7. The docking interface of embodiment 6, wherein:
   in response to detecting a number of one or more reflected optical signals during the docking event, the at least one processor is configured to disable the transceiver, and in response to detecting at least one optical signal transmitted by the other device during the docking event, the at least one processor is configured to establish an optical communication link with the other device.

8. The docking interface of embodiment 6, wherein:
in response to detecting a predetermined percentage of the transmitted optical signals as reflected optical signals during the docking event, the at least one processor is configured to disable the transceiver, and
in response to detecting at least one optical signal transmitted by the other device during the docking event, the at least one processor is configured to establish an optical communication link with the other device.

9. The docking interface of embodiment 8, wherein the predetermined percentage is at least 80%.

10. The docking interface of embodiment 1, wherein, in response to detecting the undocking event when the magnitude of the electrical signal is less than the proximity threshold value, the at least one processor is configured to enable the transceiver to transmit optical signals.

11. The docking interface of embodiment 10, wherein:
in response to enabling the transceiver during the undocking event, the at least one processor is configured to monitor for received optical signals that are received at the transceiver, and
in response to not receiving received optical signals at the transceiver within a predetermined time period after enabling the transceiver during the undocking event, the at least one processor is configured to disable the transceiver.

12. The docking interface of embodiment 1, further comprising:
a magnet configured to produce a magnetic field that is detectable by a magnetic field sensor element of the other device.

13. A docking interface configured to dock with another device, comprising:
a power supply;
a power contact configured to be selectively connected and disconnected to the power supply;
a magnetic field sensor element configured to generate an electrical signal in response to a magnetic field impinging thereon;
at least one processor configured to receive the electrical signal, compare a magnitude of the electrical signal to a proximity threshold value to generate a comparison result, and detect a docking event and an undocking event based on the comparison result,
wherein the at least one processor is configured to connect the power contact to the power supply in response to detecting the docking event to enable power to be distributed to the other device, and
wherein the at least one processor is configured to disconnect the power contact from the power supply in response to detecting the undocking event.

14. The docking interface of embodiment 13, wherein:
the at least one processor is configured to detect the docking event in response to the comparison result indicating that the magnitude of the electrical signal has increased such that it has become equal to or greater than the proximity threshold value, and
the at least one processor is configured to detect the undocking event in response to the comparison result indicating that the magnitude of the electrical signal has decreased such that it has become less than the proximity threshold value.

15. The docking interface of embodiment 14, further comprising:
a docked signal contact configured to transmit a docked signal to the other device indicating that the docking interface is fully docked with the other device,
wherein, in response to detecting the docking event, the at least one processor is configured to generate the docked signal and provide the docked signal to the docked signal contact, and
wherein, in response to detecting the undocking event, the at least one processor is configured to cease generating the docked signal.

16. The docking interface of embodiment 14, further comprising:
an optical link module comprising a transceiver configured to transmit and receive optical signals;
wherein, in response to detecting the docking event, the at least one processor is configured to enable the transceiver to transmit optical signals.

17. The docking interface of embodiment 16, wherein:
in response to enabling the transceiver during the docking event, the at least one processor is configured to monitor for reflected optical signals corresponding to the transmitted optical signals, the reflected optical signals being received at the transceiver, and
in response to detecting a number of one or more reflected optical signals during the docking event, the at least one processor is configured to disable the transceiver.

18. The docking interface of embodiment 14, further comprising:
a reflective structure arranged in an optical transmission path of the other device, where the reflective structure is configured to reflect optical signals received from the other device as reflected optical signals.

19. The docking interface of embodiment 13, further comprising:
a magnet configured to produce a magnetic field that is detectable by a magnetic field sensor element of the other device.

20. A docking interface configured to dock with another device, comprising:
a rechargeable power supply;
a power contact configured to be selectively connected and disconnected to the rechargeable power supply;
a power distribution controller configured to monitor a value of a power signal received at the power contact, including comparing the value to a threshold value to generate a comparison result and determining whether or not the docking interface is docked with the other device based on the comparison result,
wherein, in response to the value being equal or greater than the threshold value, the power distribution controller is further configured to connect the power contact to the rechargeable power supply to enable power to be distributed from the other device to the rechargeable power supply via the power contact to recharge the rechargeable power supply, and
wherein, in response to the value being less than the threshold value, the power distribution controller is further configured to disconnect the power contact from the rechargeable power supply.

21. The docking interface of embodiment 20, further comprising:
an optical link module comprising a transceiver configured to transmit and receive optical signals; and a magnetic field sensor element configured to generate an electrical signal in response to a magnetic field impinging thereon, wherein the at least one processor is configured to receive the electrical signal, compare a magnitude of the electrical signal to a proximity threshold value to generate a comparison result, and detect a docking event and an undocking event based on the comparison result.

22. The docking interface of embodiment 21, wherein:

the at least one processor is configured to detect the docking event in response to the comparison result indicating that the magnitude of the electrical signal has increased such that it has become equal to or greater than the proximity threshold value, and the at least one processor is configured to detect the undocking event in response to the comparison result indicating that the magnitude of the electrical signal has decreased such that it has become less than the proximity threshold value.

23. The docking interface of embodiment 22, wherein, in response to detecting the docking event, the at least one processor is configured to enable the transceiver to transmit optical signals.

24. The docking interface of embodiment 23, wherein:

in response to enabling the transceiver during the docking event, the at least one processor is configured to monitor for reflected optical signals corresponding to the transmitted optical signals, the reflected optical signals being received at the transceiver, and in response to detecting a number of one or more reflected optical signals during the docking event, the at least one processor is configured to disable the transceiver.

25. The docking interface of embodiment 20, further comprising:

a reflective structure arranged in an optical transmission path of the other device, where the reflective structure is configured reflect optical signals received from the other device as reflected optical signals.

26. The docking interface of embodiment 20, further comprising:

a magnet configured to produce a magnetic field that is detectable by a magnetic field sensor element of the other device.

27. A docking interface configured to dock with another device, comprising:

a rechargeable power supply;

a power contact configured to be selectively connected and disconnected to the rechargeable power supply;

a docked signal contact configured to receive a docked signal from the other device indicating that the docking interface is docked with the other device; and at least one processor configured to selectively connect and disconnect the power contact to the rechargeable power supply based on detecting the docked signal, wherein, in response to detecting the docked signal, the at least one processor is configured to connect the power contact to the rechargeable power supply to enable power to be distributed from the other device to the rechargeable power supply via the power contact to recharge the rechargeable power supply, and wherein, in response to not detecting the docked signal, the at least one processor is configured to disconnect the power contact from the rechargeable power supply.

28. The docking interface of embodiment 27, further comprising:

an optical link module comprising a transceiver configured to transmit and receive optical signals; and a magnetic field sensor element configured to generate an electrical signal in response to a magnetic field impinging thereon, wherein the at least one processor is configured to receive the electrical signal, compare a magnitude of the electrical signal to a proximity threshold value to generate a comparison result, and detect a docking event and an undocking event based on the comparison result.

29. The docking interface of embodiment 28, wherein:

the at least one processor is configured to detect the docking event in response to the comparison result indicating that the magnitude of the electrical signal is equal to or greater than the proximity threshold value, and the at least one processor is configured to detect the undocking event in response to the comparison result indicating that the magnitude of the electrical signal is less than the proximity threshold value.

30. The docking interface of embodiment 29, wherein, in response to detecting the docking event, the at least one processor is configured to enable the transceiver to transmit optical signals.

31. The docking interface of embodiment 30, wherein:

in response to enabling the transceiver during the docking event, the at least one processor is configured to monitor for reflected optical signals corresponding to the transmitted optical signals, the reflected optical signals being received at the transceiver, and in response to detecting a number of one or more reflected optical signals during the docking event, the at least one processor is configured to disable the transceiver.

32. The docking interface of embodiment 27, further comprising:

a reflective structure arranged in an optical transmission path of the other device, where the reflective structure is configured reflect optical signals received from the other device as reflected optical signals.

33. The docking interface of embodiment 27, further comprising:

a magnet configured to produce a magnetic field that is detectable by a magnetic field sensor element of the other device.

34. A method of docking a docking interface with another device, the method comprising:

generating an electrical signal in response to a magnetic field impinging a magnetic field sensor element;

comparing a magnitude of the electrical signal to a proximity threshold value to generate a comparison result;

detecting a docking event and an undocking event based on the comparison result;

in response to detecting the docking event when the magnitude of the electrical signal is greater than the proximity threshold value, enabling a transceiver to transmit optical signals, in response to enabling the transceiver during the docking event, monitoring for reflected optical signals corresponding to the transmitted optical signals, the reflected optical signals being received at the transceiver; and in response to detecting a number of one or more reflected optical signals during the docking event, disabling the transceiver.

35. The method of embodiment 34, wherein the number of reflected optical signals is greater than one.

36. The method of embodiment 34, wherein:
in response to enabling the transceiver during the docking event, monitoring for optical signals transmitted by the other device, the optical signals being received at the transceiver; and
in response to detecting at least one optical signal transmitted by the other device during the docking event, establishing an optical communication link with the other device.

37. The method of embodiment 34, wherein:
in response to enabling the transceiver during the docking event, monitoring for received optical signals that are received at the transceiver and determining whether the received optical signals are reflected optical signals corresponding to the transmitted optical signals or optical signals transmitted by the other device.

38. The method of embodiment 37, wherein:
in response to detecting a number of one or more reflected optical signals during the docking event, disabling the transceiver; and
in response to detecting at least one optical signal transmitted by the other device during the docking event, establishing an optical communication link with the other device.

39. The method of embodiment 37, wherein:
in response to detecting a predetermined percentage of the transmitted optical signals as reflected optical signals during the docking event, disabling the transceiver; and
in response to detecting at least one optical signal transmitted by the other device during the docking event, establishing an optical communication link with the other device.

40. The method of embodiment 39, wherein the predetermined percentage is at least 80%.

41. The method of embodiment 34, wherein, in response to detecting the undocking event when the magnitude of the electrical signal is less than the proximity threshold value, enabling the transceiver to transmit optical signals.

42. The method of embodiment 41, wherein:
in response to enabling the transceiver during the undocking event, monitoring for received optical signals that are received at the transceiver; and
in response to not receiving received optical signals at the transceiver within a predetermine time period after enabling the transceiver during the undocking event, disabling the transceiver.

43. The method of embodiment 34, further comprising:
producing a magnetic field that is detectable by a magnetic field sensor element of the other device.

44. A method of docking a docking interface with another device, the method comprising:
generating, by a magnetic field sensor element integrated at the docking interface, an electrical signal in response to a magnetic field impinging thereon;
at least one processor configured to receive the electrical signal, compare a magnitude of the electrical signal to a proximity threshold value to generate a comparison result, and detect a docking event and an undocking event based on the comparison result; and
selectively connecting and disconnecting a power contact integrated at the docking interface with a power supply based on detecting the docking event and an undocking event, including connecting the power contact to the power supply,
wherein the power contact is connected to the power supply in response to detecting the docking event to enable power to be distributed to the other device, and wherein the power contact is disconnected from the power supply in response to detecting the undocking event.

45. A method of docking a docking interface with another device, the method comprising:
monitoring a value of a power signal received at a power contact that is integrated at the docking interface, including comparing the value to a threshold value to generate a comparison result and determining whether or not the docking interface is docked with the other device based on the comparison result;
in response to the value being equal or greater than the threshold value, connect the power contact to a rechargeable power supply to enable power to be distributed from the other device to the rechargeable power supply via the power contact to recharge the rechargeable power supply; and
in response to the value being less than the threshold value, disconnecting the power contact from the rechargeable power supply.

While various embodiments have been disclosed, it will be apparent to those skilled in the art that various changes and modifications can be made which will achieve some of the advantages of the concepts disclosed herein without departing from the spirit and scope of the present disclosure. It will be obvious to those reasonably skilled in the art that other components performing the same functions may be suitably substituted. It is to be understood that other embodiments may be utilized and structural or logical changes may be made without departing from the scope of the present disclosure. It should be mentioned that features explained with reference to a specific figure may be combined with features of other figures, even in those not explicitly mentioned. Such modifications to the general inventive concept are intended to be covered by the appended claims and their legal equivalents.

Furthermore, the following claims are hereby incorporated into the detailed description, where each claim may stand on its own as a separate example embodiment. While each claim may stand on its own as a separate example embodiment, it is to be noted that—although a dependent claim may refer in the claims to a specific combination with one or more other claims-other example embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods. For example, the techniques described in this disclosure may be implemented, at least in part, in hardware, software, firmware, or any combination thereof. For example, various aspects of the described techniques may be implemented within one or more processors, including one or more microprocessors, DSPs, ASICs, or any other equivalent integrated or discrete logic circuitry, as well as any combinations of such components.

Further, it is to be understood that the disclosure of multiple acts or functions disclosed in the specification or in the claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. A docking interface configured to dock with another device, comprising:
   an optical link module comprises a transceiver configured to transmit and receive optical signals and to generate electrical signals therefrom;
   at least one processor configured to receive the electrical signal, compare a magnitude of the electrical signal to a proximity threshold value to generate a comparison result, and detect a docking event and an undocking event based on the comparison result; and
   a reflective structure configured to be arranged in an optical transmission path of the other device, where the reflective structure is configured to reflect optical signals received from the other device as reflected optical signals,
   wherein the at least one processor is configured to associate the magnitude of the electrical signal with one of a docking event and an undocking event.

2. The docking interface of claim 1, wherein:
   in response to detecting the docking event, the at least one processor is configured to enable the transceiver to transmit optical signals;
   in response to enabling the transceiver during the docking event, the at least one processor is configured to monitor for optical signals transmitted by the other device, the optical signals being received at the transceiver, and
   in response to detecting at least one optical signal transmitted by the other device during the docking event, the at least one processor is configured to establish an optical communication link with the other device.

3. The docking interface of claim 1, wherein:
   in response to detecting the docking event, the at least one processor is configured to enable the transceiver to transmit optical signals;
   in response to enabling the transceiver during the docking event, the at least one processor is configured to monitor for reflected optical signals corresponding to the transmitted optical signals, the reflected optical signals being received at the transceiver, and
   in response to detecting a number of one or more reflected optical signals during the docking event, the at least one processor is configured to disable the transceiver.

4. The docking interface of claim 3, wherein the number of reflected optical signals is greater than one.

5. The docking interface of claim 1, wherein:
   in response to detecting the docking event, the at least one processor is configured to enable the transceiver to transmit optical signals; and
   in response to enabling the transceiver during the docking event, the at least one processor is configured to monitor for received optical signals that are received at the transceiver and determine whether the received optical signals are reflected optical signals corresponding to the transmitted optical signals or optical signals transmitted by the other device.

6. The docking interface of claim 5, wherein:
   in response to detecting a number of one or more reflected optical signals during the docking event, the at least one processor is configured to disable the transceiver, and
   in response to detecting at least one optical signal transmitted by the other device during the docking event, the at least one processor is configured to establish an optical communication link with the other device.

7. The docking interface of claim 5, wherein:
   in response to detecting a predetermined percentage of the transmitted optical signals as reflected optical signals during the docking event, the at least one processor is configured to disable the transceiver, and
   in response to detecting at least one optical signal transmitted by the other device during the docking event, the at least one processor is configured to establish an optical communication link with the other device.

8. The docking interface of claim 7, wherein the predetermined percentage is at least 80%.

9. The docking interface of claim 1, wherein, in response to detecting the undocking event when the magnitude of the electrical signal is less than the proximity threshold value, the at least one processor is configured to enable the transceiver to transmit optical signals.

10. The docking interface of claim 9, wherein:
    in response to enabling the transceiver during the undocking event, the at least one processor is configured to monitor for received optical signals that are received at the transceiver, and
    in response to not receiving received optical signals at the transceiver within a predetermined time period after enabling the transceiver during the undocking event, the at least one processor is configured to disable the transceiver.

11. The docking interface of claim 1, further comprising a magnetic field sensor element configured to generate an electrical signal in response to a magnetic field impinging thereon.

12. The docking interface of claim 11, further comprising:
    a magnet configured to produce a magnetic field that is detectable by a magnetic field sensor element of the other device.

13. A docking interface configured to dock with another device, comprising:
    a power supply;
    a power contact configured to be selectively connected and disconnected to the power supply;
    a magnetic field sensor element configured to generate an electrical signal in response to a magnetic field impinging thereon;
    at least one processor configured to receive the electrical signal, compare a magnitude of the electrical signal to a proximity threshold value to generate a comparison result, and detect a docking event and an undocking event based on the comparison result.

14. The docking interface of claim 13, further comprising:
    a magnet configured to produce a magnetic field that is detectable by a magnetic field sensor element of the other device.

15. The docking interface of claim 13, wherein:
    the at least one processor is configured to detect the docking event in response to the comparison result indicating that the magnitude of the electrical signal has increased such that it has become equal to or greater than the proximity threshold value, and
    the at least one processor is configured to detect the undocking event in response to the comparison result indicating that the magnitude of the electrical signal has decreased such that it has become less than the proximity threshold value.

16. The docking interface of claim 15, further comprising:
    a docked signal contact configured to transmit a docked signal to the other device indicating that the docking interface is fully docked with the other device, wherein, in response to detecting the docking event, the at least one processor is configured to generate the docked signal and provide the docked signal to the docked signal contact, and wherein, in response to detecting the undocking event, the at least one processor is configured to cease generating the docked signal.

17. The docking interface of claim 15, further comprising:
an optical link module comprising a transceiver configured to transmit and receive optical signals;
wherein, in response to detecting the docking event, the at least one processor is configured to enable the transceiver to transmit optical signals.

18. The docking interface of claim 17, wherein:
in response to enabling the transceiver during the docking event, the at least one processor is configured to monitor for reflected optical signals corresponding to the transmitted optical signals, the reflected optical signals being received at the transceiver, and
in response to detecting a number of one or more reflected optical signals during the docking event, the at least one processor is configured to disable the transceiver.

19. A docking interface configured to dock with another device, comprising:
a rechargeable power supply;
an electrical contact configured to be selectively connected and disconnected to the rechargeable power supply;
a controller configured to monitor a value of a current signal received at the electrical contact, including comparing the value to a threshold value to generate a comparison result and determining whether or not the docking interface is docked with the other device based on the comparison result,
wherein, in response to the value being equal or greater than the threshold value, the controller is further configured to connect the electrical contact to the rechargeable power supply to enable power to be distributed from the other device to the rechargeable power supply via the electrical contact to recharge the rechargeable power supply, and
wherein, in response to the value being less than the threshold value, the controller is further configured to disconnect the electrical contact from the rechargeable power supply.

* * * * *